(12) United States Patent
Briggs et al.

(10) Patent No.: US 7,674,584 B2
(45) Date of Patent: *Mar. 9, 2010

(54) METHOD FOR MEASURING BINDING OF A TEST COMPOUND TO A G-PROTEIN COUPLED RECEPTOR

(75) Inventors: Mark Samuel Briggs, Cardiff (GB); Albert Francis Santos, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/576,194

(22) PCT Filed: Sep. 27, 2005

(86) PCT No.: PCT/GB2005/003688

§ 371 (c)(1),
(2), (4) Date: Apr. 30, 2007

(87) PCT Pub. No.: WO2006/035208

PCT Pub. Date: Apr. 6, 2006

(65) Prior Publication Data

US 2007/0218520 A1    Sep. 20, 2007

(30) Foreign Application Priority Data

Sep. 30, 2004 (GB) .................. 0421693.3

(51) Int. Cl.
*C12Q 1/68* (2006.01)
*G01N 33/53* (2006.01)

(52) U.S. Cl. ................. 435/6; 435/7.1; 435/7.2
(58) Field of Classification Search .............. None
See application file for complete search history.

(56) References Cited

U.S. PATENT DOCUMENTS

| 6,140,087 A | 10/2000 | Graham et al. |
| 6,448,377 B1 | 9/2002 | Kobilka et al. |

FOREIGN PATENT DOCUMENTS

| WO | WO 97/48820 | 12/1997 |
| WO | WO 98/16557 | 4/1998 |
| WO | WO02/36622 | 5/2002 |
| WO | WO02/077200 | 10/2002 |
| WO | WO02/092831 | 11/2002 |
| WO | WO02/099424 | 12/2002 |
| WO | WO02/099432 | 12/2002 |
| WO | WO03/008435 | 1/2003 |
| WO | WO03/013551 | 2/2003 |
| WO | WO03/040303 | 5/2003 |
| WO | WO2004/035614 | 4/2004 |
| WO | WO2005/003685 | 1/2005 |
| WO | WO2005/108994 | 11/2005 |

OTHER PUBLICATIONS

Sarvazyan et al., Fluoresence analysis of receptor—G protein interactions in cell membranes, Biochemistry, 2002, 41: 12858-12867.*
Frang et al., Nonradioactive GTP binding assay to monitor activation of g protein-coupled receptors, Assay Drug Dev Technol., 2003, 1(2):275-280.*
Anetopoulos, et al. Receptor-Mediated Activation of Heterotrimeric G-Proteins in Living Cells, Science 291, 2408-2411, 2001.*
Kasila et al. Time-Resolved Fluorescence Based GTP Binding Assay for Gs-Protein Coupled ReceptorsRetrieved from Internet: <https://las.perkinelmer.com/Content/RelatedMaterials/Posters/PSH_TRFBasedGTPBindingAssay.pdf>.*
Ferguson, et al. (Journal of Neuroscience Methods, 109, 2001, pp. 81-89).*
Bieri, C., Ernst, O. P., Heyse, S., Hofmann, K. P. & Vogel, H. (Nov. 1999). Micropatterned Immobilization Of A G Protein-Coupled Receptor Activation. Nature Biotechnology, 17, 1105-1108.
Leaney, J., Benians, A., Graves, F. M., & Tinker, A. (Aug. 9, 2002). A Novel Strategy to Engineer Functional Fluorescent Inhibitory G-protein α Subunits. The Journal of Biological Chemistry, 277(32), 28803-28809.
Simons, P. C., Shi, M., Foutz, T., Cimino, D. F., Lewis, J., Buranda, T., Lim, W. K., Neubig, R. R., McIntire, W. E., Garrison, J., Prossnitz, E & Sklar, L. A. (2003). Molecular Pharmacology, 64(5), 1227-1238.
McEwen, D., et al., "Fluorescent BODIPY-GTP Analogs: Real-Time Measurement of Nucleotide Binding to G Proteins", Analytical Biochemistry, vol. 291, 109-117 (2001).

* cited by examiner

Primary Examiner—Suzanne M. Noakes
Assistant Examiner—Jae W Lee
(74) Attorney, Agent, or Firm—Yonggang Ji

(57) ABSTRACT

The invention provides a method for measuring binding of a test compound to a G-Protein Coupled Receptor (GPCR). The invention also provides a method for identifying and measuring the effect that an agent has upon modulating the binding of a test compound to a G-Protein Coupled Receptor.

26 Claims, 6 Drawing Sheets

Figure 4a

```
ATGACTCTTGAATCTATTATGGCTTGTTGTCTTTCTGAAGAAGCTAAAGAAGCTCGTCGT
ATTAATGATGAAATTGAACGTCAACTTCGTCGTGATAAACGTGATGCTCGTCGTGAACTT
AAACTTCTTCTTCTTGGTACTGGTGAATCTGGTAAATCTACTTTTATTAAACAAATGCGT
ATTATTCATGGTTCTGGTTATTCTGATGAAGATAAACGTGGTTTTACTAAACTTGTTTAT
CAAAATATTTTTACTGCTATGCAAGCTATGATTCGTGCTATGGATACTCTTAAAATTCCT
TATAAATATGAACATAATAAAGCTCATGCTCAACTTGTTCGTGAAGTTGATGTTGAAAAA
GTTTCTGCTTTTGAAAATCCTTATGTTGATGCTATTAAATCTCTTTGGAATGATCCTGGT
ATTCAAGAATGTTATGATCGTCGTCGTGAATATCAACTTTCTGATTCTACTAAATATTAT
CTTAATGATCTTGATCGTGTTGCTGATCCTGCTTATCTTCCTACTCAACAAGATGTTCTT
CGTGTTCGTGTTCCTACTACTGGTATTATTGAATATCCTTTTGATCTTCAATCTGTTATT
TTTCGTATGGTTGATGTTGGTGGTCAACGTTCTGAACGTCGTAAATGGATTCATTGTTTT
GAAAATGTTACTTCTATTATGTTTCTTGTTGCTCTTTCTGAATATGATCAAGTTCTTGTT
GAATCTGATAATGAAAATCGTATGGAAGAATCTAAAGCTCTTTTTCGTACTATTATTACT
TATCCTTGGTTTCAAAATTCTTCTGTTATTCTTTTTCTTAATAAAAAAGATCTTCTTGAA
GAAAAAATTATGTATTCTCATCTTGTTGATTATTTTCCTGAATATGATGGTCCTCAACGT
GATGCTCAAGCTGCTCGTGAATTTATTCTTAAAATGTTTGTTGATCTTAATCCTGATTCT
GATAAAATTATTTATTCTCATTTTACTTGTGCTACTGATACTGAAAATATTCGTTTTGTT
TTTGCTGCTGTTAAAGATACTATTCTTCAACTTAATCTTAAAGAATATAATCTTGTT
```

Figure 4b

```
MTLESIMACCLSEEAKEARRINDEIERQLRRDKRDARRELKLLLLGTGESGKSTFIKQMRIIHGSG
YSDEDKRGFTKLVYQNIFTAMQAMIRAMDTLKIPYKYEHNKAHAQLVREVDVEKVSAFENPYVD
AIKSLWNDPGIQECYDRRREYQLSDSTKYYLNDLDRVADPAYLPTQQDVLRVRVPTTGIIEYPFD
LQSVIFRMVDVGGQRSERRKWIHCFENVTSIMFLVALSEYDQVLVESDNENRMEESKALFRTIIT
YPWFQNSSVILFLNKKDLLEEKIMYSHLVDYFPEYDGPQRDAQAAREFILKMFVDLNPDSDKIIY
SHFTCATDTENIRFVFAAVKDTILQLNLKEYNLV
```

METHOD FOR MEASURING BINDING OF A TEST COMPOUND TO A G-PROTEIN COUPLED RECEPTOR

CROSS REFERENCE TO RELATED APPLICATIONS

This application is a filing under 35 U.S.C. §371 and claims priority to international patent application number PCT/GB2005/003688 filed Sep. 27, 2005, published on Apr. 6, 2006, as WO 2006/035208, which claims priority to patent application number 0421693.3 filed in Great Britain on Sep. 30, 2004; the disclosures of which are incorporated herein by reference in their entireties.

FIELD OF INVENTION

The invention relates to a method for measuring binding of a test compound to a G-Protein Coupled Receptor (GPCR). The invention also relates to a method for identifying and measuring the effect that an agent has on modulating the binding of a test compound to a GPCR.

BACKGROUND OF THE INVENTION

G-Protein Coupled Receptors (GPCRs) modulate the response of many drugs, hormones and neurotransmitters in biology. Many disorders and diseases are equally focussed around GPCR function, with therapeutics based on altering the responsivity of GPCR function by use of small ligands or peptides, acting as either agonists or antagonists.

More than 30% of all currently prescribed pharmaceutical drugs involve GPCR-mediated modulation, and more than 30% of all drug targets classes are aimed at understanding and modulating GPCR function.

GPCR Structure and Associated Binding Proteins

Currently, there are approximately 400 known GPCRs, characterised historically by nomenclature into Type A, (rhodopsin like), Type B (calcitonin) and Type C (metabotropic). With the advent of the sequencing of the human genome, sequence analysis and homology searching implied the presence of at least 150-200 GPCR-like proteins which currently possess no known endogenous ligands. These latter GPCRs are known as "orphan" receptors ('oGPCR', Howard et al. (2001) Trends in Pharm. Sci., 22, 132-140). In total, there are ~400-500 endogenous ligands known to function via characterised GPCRs, including those for recently "de-orphanised" GPCRs.

GPCRs are characterised by a conserved seven-transmembrane spanning motif, which comprise of protein helices linked by both intracellular and extracellular loop domains. The extracellular domains of GPCRs contain ligand docking (binding) sequences, and the intracellular loop domains (2nd and 3rd loop) are important docking sites for GPCR-associated proteins (Moro et al. (2003) Chem. Commun., 24, 2949-2956).

In Nature, the ligand-binding event, which occurs at extracellular binding sites on the GPCR, is transduced, postulated to be via resultant protein conformational shifts, into the intracellular matrix. The transduction mechanism is signalled via an "early event" intracellular exchange of guanosine diphosphate (GDP) for GTP (guanosine triphosphate). GDP is present at the "resting", or "ligand-unoccupied" state, and exchange for GTP occurs at the "active", or "ligand-occupied" state. The binding of either GDP or GTP occurs at defined sites of an intracellular heterotrimeric complex, known as the G-proteins, which comprise 3 subunits, $G\alpha$, $G\beta$ and $G\gamma$. GTP and GDP bind to the $G\alpha$ subunit of the heterotrimer. The G-protein complex resides on the intracellular face of membranes and is closely associated with residues within the intracellular loop domain of the GPCR. Coupling of most G protein-coupled receptors to heterotrimeric G proteins involves the third intracellular loop and the proximal region of the carboxyl-terminal tail of the GPCR.

Upon binding of GTP to the $G\alpha$ subunit, there is a resultant perturbation of the G-protein complex, which subsequently induces downstream transduction via effector systems (e.g. such as phosphatidylinositol 4,5-bisphosphate (PIP2) hydrolysis with subsequent changes in this instance, to intracellular $Ca^{2+}$ ($Ca^{2+}_i$) levels). Ligand activation may also involve internalisation of the receptor (e.g. for downstream gene induction) or direct opening of ligand-gated ion channels.

At a later stage, regardless of the precise mechanism of ligand activation, there is a need for the response to be attenuated. To "decouple" or "downregulate" the response of ligand binding to the GPCR as well as attenuate subsequent downstream transduction events, the GTP-bound to the $G\alpha$ subunit is hydrolysed by endogeneous enzymes (GTPases) back to guanosine diphosphate (GDP), leading to functional reassociation of the G-proteins and dissociation of the ligand with a return to the "resting" or "ligand-unoccupied" state.

GPCR-active ligands, and GPCR action in general, can also be characterised by the nature of the transduction event linked to $G\alpha$ functionality. $G\alpha$ functionality has been shown to be linked to primary sequences. It therefore follows that G protein classes can also be defined according to the primary sequences of their $G\alpha$ subunits. This classification has lead to definition of 4 families: $G\alpha_s$, $G\alpha_{i/o}$, $G\alpha_q$ and $G\alpha_{12/13}$.

$G\alpha_s$ ($\mu$[cAMP] via adenylate cyclase activation)
Some GPCR-active ligands can be characterised by a downstream increase in intracellular concentration of adenylate cyclase, which leads to a subsequent increase in intracellular concentrations of the important second messenger, cyclic adenosine monophosphate (cAMP). Upon ligand binding, transduction in this case is via GDP$\leftrightarrow$GTP exchange at the $G\alpha_s$ subunit.

$G\alpha_{i/o}$ ($\circ$[cAMP] via adenylate cyclase inhibition, or $K^+$ channel modulation or phosphodiesterase (PDE) activation)—Upon ligand binding, transduction occurs via GDP$\leftrightarrow$GTP exchange at the $G\alpha_i$ subunit.

$G\alpha_q$ (protein coupled, $\mu Ca^{2+}_i$ via phospholipase C beta (PLC$\beta$))
Transduction is via GDP$\leftrightarrow$GTP exchange at the $G\alpha_q$ subunit. Response is pertussis toxin sensitive. PLC$\beta$ catalyses release of diacylglycerol (DAG) and inositol 1,4,5-phosphate (IP$_3$) from inositol 4,5-diphosphate (PIP2). IP$_3$ increase is linked to $Ca^{2+}_i$ release. It has also been found that heterologous expression of $G\alpha_{16}$ (a member of $G\alpha_q$), can allow coupling of a wide range of GPCRs to PLC$\beta$ activity and allow measurements of $Ca^{2+}_i$ flux.

$G\alpha_{12/13}$ (protein coupled, interacting with $Cl^-$ channels)
Transduction is via GDP$\leftrightarrow$GTP exchange at the $G\alpha_{12/13}$ subunit Methods of Carrying Out GPCR Assays to Measure Ligand Potency There is a continuing desire within the pharmaceutical industry to exploit GPCRs and orphan GPCRs as drug targets. Many methods have been used to measure GPCR activity and in vitro assays form an important part of high throughput screening strategies in the search for new GPCR-active ligands. Complementary technologies involve cell-based assay formats in which for example, $Ca^{2+}{}_i$ flux measurement can be made within intact cells by use of calcium-sensitive fluorescent indicators. In the latter case, the use of sensitive detection platforms have been aided by the creation of chimeric G proteins (such as $G\alpha_s$-$G\alpha_q$) or the heterologous expression of $G\alpha_{16}$, to allow "forced coupling" of ligand response through PLCβ activation pathways, enabling a $Ca^{2+}{}_i$ readout to be made (Milligan & Rees (1999) Trends in Pharm. Sci., 20, 118-124).

Traditional methods of carrying out GPCR assays involve use of radioactive ligands. These are employed in heterogeneous filter-based or homogeneous SPA-based (Scintillation Proximity Assay) assays. From these studies, the end user can obtain information on ligand potency by measurement of the radioactive counts on the filter (after separation of bound from free ligand) or directly on the SPA bead.

Use of Radioactive [$^{35}$S]GtpγS

To exploit the binding of GTP to Gα as a high sensitivity in vitro assay interrogation point, researchers have developed GTPase-resistant ("non-hydrolysable") analogues of GTP, with one of the most efficacious being radioactive [$^{35}$S]GTPγS (Milligan (2003) Trends in Pharm. Sci., 24, 87-90; Ferrer et al. (2003) Assay & DDT, 1, 261-273). When a non-radioactive ligand now binds to cell membranes carrying a functional GPCR [$^{35}$S]GTPγS is recruited to the G-protein Gα subunit. As [$^{35}$S]GTPγS is essentially "non-hydrolysable", the receptor/G-protein system is effectively "locked" in a ligand-occupied state. Now, radioactive filter counts or SPA counts of G-protein-bound [$^{35}$S]GTPγS allows the user to obtain information on both the ligand binding potency as well as the ligand efficacy. Use of [$^{35}$S]GTPγS in this manner means that, in essence, the user is carrying out an in vitro "functional assay". The GTP-probe is effectively acting as a post-binding event reporter, at an early position in the transduction process.

The Need for Homogeneous Fluorescence Assays for GPCRs

Whilst inherently sensitive radioactive assays (heterogeneous and homogeneous format) have formed the bulk of generic in vitro screening assays for GPCRs, there has been a desire to move towards sensitive, non-radioactive, and in particular homogeneous assays (Kimble et al., (2003) Combin.Chem & High Thr. Screening, 6, 409-418). The latter assay formats are particularly amenable to miniaturisation and hence provide time and material cost savings. A robust signal which can be easily measured on a spectrophotometer, in particular an optical signal, would be of advantage. Fluorescence intensity measurements, and in particular Fluorescence Resonance Energy Transfer (FRET), would fulfil many desirable requirements for a suitable assay format.

FRET is a distance-related process in which the electronic excited states of two dye molecules interact without emission of a photon (Forster, T., "Intermolecular Energy Transfer and Fluorescence", Ann. Physik., Vol. 2, p. 55, (1948)). One result of this interaction is that excitation of a donor molecule enhances the fluorescence emission of an acceptor molecule. The fluorescence quantum yield of the donor is correspondingly diminished. For FRET to occur, suitably, the donor and acceptor dye molecules must be in close proximity (typically between 10-100 Å), since energy transfer efficiency decreases inversely as the 6th power of the distance (r) between the donor and acceptor molecules.

In FRET, molecules which act as FRET "donors" are allowed to interact with molecules which act as FRET "acceptors". By donor, it is meant that the dye moiety is capable of absorbing energy from light and emits light at wavelength frequencies which are at least partly within the absorption spectrum of the acceptor. By acceptor, it is meant that the dye moiety is capable of absorbing energy at a wavelength emitted by a donor dye moiety.

If these donor and acceptors come into close contact within a critical distance, then FRET occurs and spectroscopic measurements taken at the emission wavelengths of the acceptor will give an indication of the magnitude of the FRET interaction. If the donor and acceptor fluors are allowed to come into close contact as a result of a biological interaction, then it follows that the magnitude of the FRET signal will be related to the magnitude of the biological interaction under scrutiny. Under suitable conditions, the closest molecular distances between the FRET partners can be calculated from the maximum FRET signal.

Fluorescent Analogues of GTP

There has always been a desire to develop non-radioactive (fluorescent) reporter analogues of [$^{35}$S]GTPγS. Many have been described in the literature, but most suffer from high rates of hydrolysis and/or poor affinity for the G-proteins (McEwen et al. (2001) Anal. Biochem., 291, 107-117); Korlach et al., (2004) Proc. Natl.Acad. Sci., 101, 2800-2805). There is, therefore, a need within the pharmaceutical industries for a hydrolytically stable fluorescent reporter analogue which has a high degree of affinity for the G-proteins. Such a reporter molecule is described herein and is the subject of the Applicant's (Amersham Biosciences UK Limited) co-pending patent application entitled 'Fluorescent Nucleotide Analogues' (WO 05/003685 claiming priority to applications GB 0421691.7 and GB 0500504.6).

Prior Art—Examples of "Intermolecular" GPCR Fret Assays

Both in vitro and cell-based GPCR FRET assays have been cited in the literature. The FRET interaction in these instances is between two interacting "partner" biological species (for example, proteins) with the "donor" and "acceptor" fluorescent molecules bound to their respective but separate, species. When the two biological partners interact, FRET can occur under controlled conditions.

As referred to herein, the term "intermolecular interactions" are described as those occurring between separate G-protein subunits, Gα, Gβ and Gγ.

Leaney et al., (J. Biol. Chem. (2002) 277, 28803-28809) describes the potential use of cyan fluorescently tagged Gα-protein subunits in FRET assays for investigating protein-protein interactions. Similarly, WO 03/008435 postulates on the use of Gα-green fluorescent protein (GFP) constructs in FRET assays for screening for GPCR drug targets. A method for detecting ligand binding using a FRET assay based upon the interaction of a blue fluorescent protein-Gα construct with a yellow fluorescent protein-Gα construct is reported in WO 02/077200 for identifying proteins involved in olfaction.

Bunemann et al., (Proc. Natl.Acad. Sci. (2003) 26, 16077-16082) describe use of cloned fluorescent protein tagged G-proteins which were viably reconstituted into cultured host human embryonic kidney (HEK) cells. G-proteins were tagged with either cyan fluorescent protein (CFP) or yellow fluorescent protein (eYFP), namely, Gαi-eYFP, Gβ1-CFP and/or Gγ2-CFP. FRET signals were observed that were ligand (agonist) dependent, and which were postulated to be as a result of G-protein conformational shifts in response to specific ligand binding, allowing a measure of both ligand binding potency as well as changes in intermolecular distances, as the ligand "on-off" cycle progresses.

Potential limitations pertaining to this latter "intermolecular" strategy is the requirement for two (or more) species to interact at appropriate times, orientations and concentrations. Significant alteration of the endogenous G-proteins by attachment of large fluorescent proteins may well lead to perturbation of the binding events under investigation. Alternatively, random chemical labelling with smaller, low molecular weight (MW) fluorescent tags can be carried out, but this may also lead to perturbation of natural biological function due to for example, unwanted chemical modifications at key binding sites and subsequent attenuation of binding affinity. There is also a real possibility of an increase in non-specific binding interactions when more than one species is required for an interaction. Also, the creation of two or more binding partners each labelled with potentially large fluorescent proteins may for example, lead to severe steric interactions leading to an attenuated or anomalous FRET response.

In addition, two biological species (G$\alpha$ and G$\beta$ or G$\gamma$ in the example cited) have to be labelled with FRET partners, and if the labelling is intrinsic, then suitable cloning vectors have to be constructed leading to the generation of two or more recombinant proteins. To counter this situation by use of extrinsic labelling strategies, each binding partner may have be individually and site-specifically chemically labelled, which may be cumbersome, due to the requirements of high chemo- and regio-selectivity control.

Blaesius et al., (Presentation Number 135 in Session on 'Assay Development and Validation Strategies', The Society for Biomolecular Screening-7$^{th}$ Annual Conference, 12 Sep. 2001) and WO 04/035614 describe another example of an "intermolecular" FRET assay for GPCRs (FIG. 1), using engineered peptide affinity probes. The authors describe the use of novel biotinylated peptide affinity probes which differentiate the GTP-bound state from the GDP-bound state of G$\alpha_i$ or G$\alpha_s$. By using a carboxy-terminal histidine-tagged (his$_6$) reconstituted GPCR, they were able to show, upon addition of suitable GPCR ligands, a detectable FRET signal between streptavidin-europium (bound to the biotin affinity peptide) and an allophycocyanin (APC)-labelled anti-histidine antibody.

A limitation pertaining to this method is the fact that the peptide affinity probe is not covalently bound to the target G$\alpha$ subunit, and therefore the relative affinities of a set of peptide probes need to be carefully evaluated for each set of G$\alpha$ species. This is an important issue, as there are multiple types of G$\alpha$s, G$\alpha$i/o and G$\alpha$q that have been identified. Screening for sets of peptide probes of sufficient affinity is a laborious process, involving many cycles of compound generation and screening, such as by phage display panning, as well as optimisation by evolved library strategies. Indeed, even after suitable screening, the affinity of the peptide probe may either be quite low or be too highly cross-reactive between G$\alpha$ species, so precluding use in an assay.

In addition, both the nature and position of binding of the probe is unknown, which is not an ideal situation when trying to optimise probe design. Another disadvantage of having a non-covalent binding probe is the risk of facile perturbation of this probe-target interaction by other factors, such as putative drugs or buffer/detergent conditions.

"Intramolecular" GPCR FRET Assays

Work by Frang et al., ('Homogeneous GTP binding assay for GPCRs based on TR-FRET', poster, SBS 9$^{th}$ Annual Conference, Portland, Oreg.), uses identical peptide affinity probe technology invented by Blaesius et al. (Karo Bio, USA Inc.) described above. Frang describes use of a biotinylated peptide sourced from Karo Bio, which is a peptide affinity probe that recognises the GTP-bound state of G$\alpha_i$. FRET occurs as a result of interaction between streptavidin-europium donor label (bound to the biotin affinity probe) and a fluorescent GTP analogue (Alexa647-GTP), which acts as a FRET acceptor.

Although the FRET response is configured around a single biological molecular entity (G$\alpha$i in this case), and can therefore be referred to as "intramolecular", the arguments cited earlier against employing the non-covalent binding of a biotinylated peptide affinity probe are still pertinent. Indeed, the arguments can be applied to any non-covalent binding approaches using any other type of probe, such as an antibody or aptamer.

The present invention seeks to address the above problems which exist in the prior art and to provide methods for detecting binding of a test compound (or ligand) to a GPCR and methods of identifying agents which modulate the binding of test compounds (or ligands) to GPCRs.

SUMMARY OF THE INVENTION

According to a first aspect of the present invention, there is provided a method for detecting binding of a test compound to a G-Protein Coupled Receptor (GPCR), the method comprising measuring the level of interaction between a first detectable group and a second detectable group by optical means wherein the method involves a G$\alpha$ subunit which comprises a covalently bound first tag capable of binding to the first detectable group; the first detectable group, and either a GTPase resistant GTP analogue having the second detectable group, or a GTPase resistant GTP analogue having a second tag capable of binding to the second detectable group.

In a second aspect of the present invention, there is provided a method for detecting binding of a test compound to a G-Protein Coupled Receptor (GPCR), the method comprising measuring the level of interaction between a first detectable group and a second detectable group by optical means the method involving a G$\alpha$ subunit which comprises the first detectable group covalently bound to the G$\alpha$ subunit and either a GTPase resistant GTP analogue having the second detectable group, or a GTPase resistant GTP analogue having a second tag capable of binding to the second detectable group.

Suitably, the method of the first or second aspect involves use of a reaction mixture comprising at least one of the following reagents:

i) a test compound ii) a second detectable group.

Suitably, the method of the first aspect comprises the steps of:

i) contacting the GPCR with the test compound ii) contacting the G$\alpha$ subunit with the GTPase resistant GTP analogue having a second detectable group iii) binding the first detectable group to the covalently bound first tag, and iv) detecting a signal wherein the sequence of steps ii) and iii) is interchangeable.

Suitably, the method of the second aspect comprises the steps of:

i) contacting the GPCR with the test compound ii) contacting the G$\alpha$ subunit with the GTPase resistant GTP analogue having a second detectable group, and iii) detecting a signal.

Suitably, the method of the first aspect comprises the steps of:
i) contacting the GPCR with the test compound
ii) contacting the Gα subunit with the GTPase resistant GTP analogue having a second tag capable of binding to a second detectable group
iii) binding a first detectable group to the first tag
iv) binding a second detectable group to said second tag, and
v) detecting a signal wherein step i) is the first step and step v) is the last step, the sequence of steps ii)-iv) being irrelevant.

Suitably, the method of the second aspect comprises the steps of:
i) contacting the GPCR with the test compound
ii) contacting the Gα subunit with the GTPase resistant GTP analogue having a second tag capable of binding to a second detectable group
iii) binding a second detectable group to said second tag
iv) detecting a signal wherein the sequence of steps ii) and iii) is interchangeable.

Suitably, the signal is compared to a signal obtained in the absence of the test compound.

Suitably, the test compound is an organic or inorganic molecule. Preferably, the organic molecule is selected from the group consisting of peptide, polypeptide, nucleotide, polynucleotide, protein nucleic acid, saccharide, polyglyceride and small organic molecule.

Preferably, the test compound is a ligand.

By establishing the use of such a strategy within the context of the first and/or second aspect of the invention, the skilled person is, for example, able to screen a number of potential natural endogenous ligands for their ability to bind to, as well as modulate downstream transduction events at a specific subtype of GPCR polypeptides. An extension of this strategy is to carry out "de-orphanising" of orphan GPCRs, whereby an orphan GPCR can be assigned to its associated endogenous ligand from both a binding and functional aspect.

Suitably, the ligand is known to bind to the GPCR polypeptide. Examples of such known ligands which bind to particular GPCR polypeptides are well known in the art.

Suitably, the method is a homogeneous method.

In a third aspect of the present invention, there is provided a method for detecting the effect an agent has upon modulating the binding of a test compound to a GPCR, said method comprising detecting the binding of said compound to said GPCR as hereinbefore described in the presence of the agent and comparing binding in the absence of the agent.

While binding of the test compound (or ligand) can be detected qualitatively, preferably binding is measured quantitatively.

By the use of such a strategy, the end user is able to assign a rank order of potency of a number of agents relative to the reference ligand. This enables identification of potentially suitable drug candidates which are able to modulate GPCR function. The agents may be single molecular entities or one of a member of a group or a cassette, for example from a natural product library or from a synthetic phage display library or from a chemically-synthesised library.

Suitably, the value of the test compound or ligand binding in the absence of the agent is already known. The term "value" can be taken to mean an actual measure of the binding affinity of a ligand, such as the molar affinity constant or molar dissociation constant. Preferably, the value of the binding in the absence of the agent is stored on an electronic database such as a computer. Optionally, the binding value in the absence of the agent may be stored on an optical database. Electronic and optical databases are configured such that data stored thereon are readily accessible, typically by data searching and 'mining' techniques well known in the art.

Suitably, the first detectable group comprises a first binding moiety which specifically binds to the first tag.

Suitably, the second detectable group comprises a second binding moiety which specifically binds to the second tag.

Suitably, the covalently bound tag and the binding moiety are members of a specific binding pair, wherein each component has a specific binding affinity for the other. Preferably, the tag and the binding moiety are selected from the group consisting of biotin/steptavidin, biotin/avidin, biotin/neutravidin, biotin/captavidin, epitope/antibody, GST/glutathione, His-tag/Nickel, FLAG/M1 antibody, maltose binding protein/maltose, chitin binding protein/chitin, calmodulin binding protein/calmodulin (Terpe, 2003, Appl Microbiol Biotechnol, 60, 523-533), Lumio™ reagents/Lumio™ recognition sequence. The Lumio™ reagents and recognition sequence (Cys-Cys-Pro-Gly-Cys-Cys) (SEQ ID NO:3). are available from Invitrogen Life Corporation, Carlsbad, Calif., USA.

Preferably, the first or second tag is poly histidine, such as $(His)_6$, and the first or second binding moiety is Nickel. More preferably, the first or second tag is FLAG and the first or second binding moiety is M1.

Most preferably, the first or second tag is biotin and the first or second binding moiety is selected from the group consisting of streptavidin, avidin, neutravidin and captavidin. Streptavidin has a high binding affinity ($10^{14}$M-$10^{-15}$M) for biotin which makes the biotin tag/steptavidin binding moiety particularly suited for the present invention. The preferred labelling position of the tag would be either at the C-terminus, or preferably at the N-terminus of the Gα subunit. One advantage of using biotin to label the Ga subunit is the small size of biotin compared, for example, with a Green Fluorescent Protein (GFP). Using a small molecule such as biotin causes less perturbation to the biological system under evaluation, compared to use of larger tags such as fluorescent-labelled proteins. In addition, use of biotin enables detection with proteins such as avidin (AV) or streptavidin (SA), which have well-documented and very high affinities ($10^{14}$M-$10^{-15}$M) for biotin. Avidin or streptavidin will be suitably labelled with a fluorescent moiety, which can act as a FRET "donor".

Suitably, the first and second detectable group is selected from the group consisting of a fluorescent moiety, a phosphorescent moiety, a luminescent moiety, and an absorbent moiety.

Suitably, the fluorescent moiety is detectable by its fluorescence properties selected from the group consisting of fluorescence emission intensity, fluorescence lifetime (FL), and fluorescence resonance energy transfer (FRET).

Preferably, the first detectable group and the second detectable group comprise fluorescent moieties which form a FRET pair, wherein the FRET pair comprises a donor FRET label and an acceptor FRET label.

Suitably, the donor FRET label is a xanthine dye or a cyanine dye.

Alternatively, the donor FRET label is a luminescent d-block and f-block metal containing complex, co-ordination compound or organometallic species.

Suitably, the donor dye is a xanthene dye, rhodamine dye or a cyanine dye and the acceptor dye is a xanthene dye, rhodamine or a cyanine dye as described in WO 05/108994 'Fluorescence Resonance Energy Transfer Enzyme Substrates'.

In one embodiment, at least one of said donor and acceptor dye moiety is a cyanine dye. In another embodiment, the donor dye is a xanthene dye and the acceptor dye is a rhodamine dye.

Suitable xanthene dyes include but are not limited to fluorescein and its derivatives and analogues, such as 5-carboxyfluorescein, 6-carboxyfluorescein and 6-carboxy-4',5'-dichloro-2',7'-dimethoxyfluorescein.

Suitable cyanine dyes include but are not limited to CyA (3-(ε-carboxypentyl)-3'-ethyl-5,5'-dimethyl oxacarbocyanine), Cy2 (3-(ε-carboxypentyl)-3'-ethyl-oxa-carbocyanine), Cy3 (3-(ε-carboxypentyl)-1'-ethyl-3,3,3',3'-tetramethyl-5,5'-disulphonato-carbocyanine), Cy3.5 (3-(ε-carboxypentyl)-1'-ethyl-3,3,3',3'-tetramethyl-4,5,4',5'-(1,3-disulphonato)dibenzo-carbocyanine), Cy5 (1-(ε-carboxypentyl)-1'-ethyl-3,3,3',3'-tetramethyl-5,5'-disulphonato-dicarbocyanine), Cy5.5 (1-(ε-carboxypentyl)-1'-ethyl-3,3,3',3'-tetramethyl-4,5,4',5'-(1,3-disulphonato)-dibenzo-dicarbocyanine), and Cy7 (1-(ε-carboxypentyl)-1'-ethyl-3,3,3',3'-tetramethyl-5,5'-disulphonato-tricarbocyanine).

The preferred label is Cy3B (i.e. 6,7,9,10-Tetrahydro-2-carboxymethyl-14-sulphonato-16, 16, 18, 18-tetramethyl-7aH-bisindolinium[3,2-a,3',2'-a]pyrano[3,2-c; 5,6-c']dipyridin-5-ium trifluoroacetate) but options can include other suitable donor labels or fluors, such as europium or terbium containing species. To improve FRET efficiency, the preferred embodiment allows optimisation of the dye-labelling stoichiometry on steptavidin or avidin.

In a preferred embodiment, the first detectable group is Cy3B-streptavidin. A standard range of dye labelling is usually one to three dye molecules per molecule of streptavidin (or avidin).

Suitably, the acceptor dye is a rhodamine dye or a cyanine dye.

Suitable rhodamine acceptor dyes include but are not limited to: 5-carboxyrhodamine (Rhodamine 110-5), 6-carboxyrhodamine (Rhodamine 110-6), 5-carboxyrhodamine-6G (R6G-5 or REG-5), 6-carboxyrhodamine-6G (R6G-6 or REG-6), N,N,N',N'-tetramethyl-5-carboxyrhodamine, N,N,N',N'-tetramethyl-6-carboxyrhodamine (TAMRA or TMR), 5-carboxy-X-rhodamine and 6-carboxy-X-rhodamine (ROX). Other classes of dyes include BODIPY™, porphyrin dyes, rhodol dyes, oxazine dyes and perylene dyes.

Suitable cyanine dyes include but are not limited to CyA (3-(ε-carboxypentyl)-3'-ethyl-5,5'-dimethyl oxacarbocyanine), Cy2 (3-(ε-carboxypentyl)-3'-ethyl-oxa-carbocyanine), Cy3 (3-(ε-carboxypentyl)-1'-ethyl-3,3,3',3'-tetramethyl-5,5'-disulphonato-carbocyanine), Cy3.5 (3-(ε-carboxypentyl)-1'-ethyl-3,3,3',3'-tetramethyl-4,5,4',5'-(1,3-disulphonato)dibenzo-carbocyanine), Cy5 (1-(ε-carboxypentyl)-1'-ethyl-3,3,3',3'-tetramethyl-5,5'-disulphonato-dicarbocyanine), Cy5.5 (1-(ε-carboxypentyl)-1'-ethyl-3,3,3',3'-tetramethyl-4,5,4',5'-(1,3-disulphonato)-dibenzo-dicarbocyanine), and Cy7 (1-(ε-carboxypentyl)-1'-ethyl-3,3,3',3'-tetramethyl-5,5'-disulphonato-tricarbocyanine).

Preferably, the cyanine dye is a pentamethine cyanine dye.

It will be understood by one skilled in the art, that specific FRET donor/acceptor pairs must be selected based upon their particular emission and absorption characteristics.

The preferred acceptor label is Cy5.

Preferably, the GTPase resistant GTP analogue is Cy5-GTP. Most preferably, the Cy5-GTP analogue is a compound having formula I or II.

Compound 1 or Formula 1

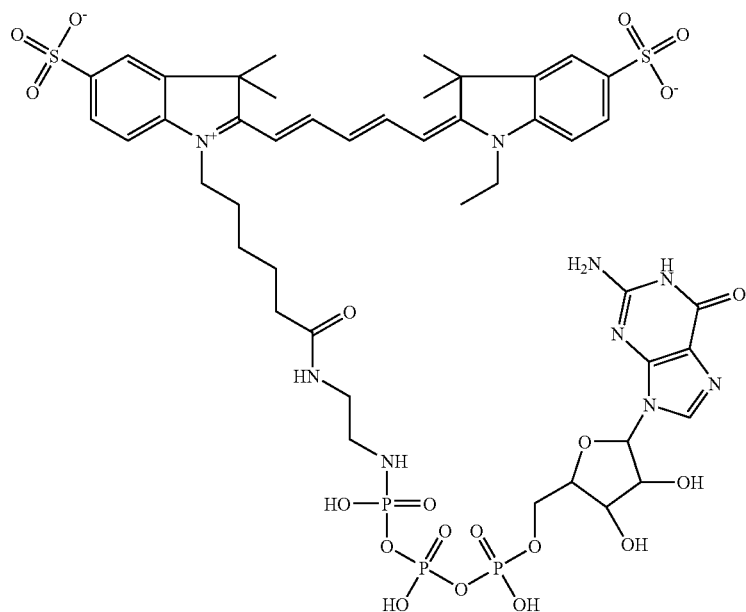

-continued

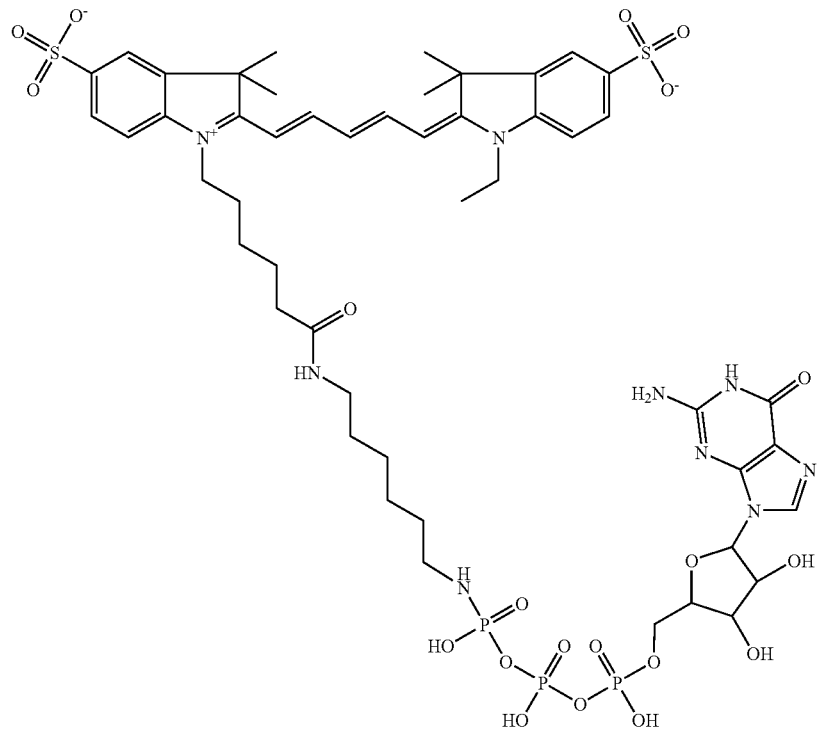

Compound 3 or Formula II

In one embodiment, the GTPase resistant analogue comprises a biotin tag. In this embodiment, the second detectable group could comprise, for example, a Cy5-streptavidin dye wherein the streptavidin binding moiety specifically binds to the biotin tag.

In a preferred embodiment, the covalently bound first tag is biotin, the GTPase resistant GTP analogue is Cy5-GTP and the first detectable group is Cy3B-Streptavidin. Thus, upon addition of a GPCR-active ligand (which may be a known or Reference ligand or a suitable candidate) which binds to and activates the GPCR, Cy5-GTP is recruited to the Gα subunit, whereupon the binding of Cy5-GTP to the target subunit is maintained due to the GTPase-resistant properties of the specifically engineered GTP analogue. Subsequent addition of the Cy3B-Streptavidin detectable group can enable the "donor" fluor (Cy3B, in this case) to be in close proximity (for example within 5 nm) of the bound "acceptor" fluor (Cy5-GTP, in this example). Upon light excitation at the wavelength of the donor fluor, FRET occurs which can be detected at the acceptor fluor emission wavelength.

In another embodiment, the covalently bound first detectable group is Cy3B and the GTPase resistant GTP analogue is Cy5-GTP.

The magnitude of the FRET response (signal in presence of ligand) minus "basal" (signal in absence of ligand) allows determination of the potency of binding and the efficacy of the GPCR ligand under investigation.

Suitably, the ligand is a natural substrate or a synthetic substrate. This 'known' ligand will have well-characterised and measured GPCR binding properties, such as binding affinity, on/off kinetic binding rates and pharmacological response.

Suitably, the agent, which may also be an unknown or candidate ligand in its own right, is selected from the group consisting of agonist, antagonist and inverse agonist. The agent may be applied in the form of a group, library or cassette containing a plurality of such agents. The agent could also refer to a suitable environmental stimulus, such as induction of changes in temperature, pressure, ionic strength and pH. In addition, the agent could comprise a chemical entity which does not operate via a GPCR transduction system, but which indirectly affects an aspect of GPCR functionality. An example of the latter may be a protein synthesis inhibitor, functional antibody, or gene "knockdown" reagent (such as sRNAi or an antisense gene).

As described herein, an agonist is any ligand (especially a drug or hormone) that binds to a receptor to alter the proportion that is in an active form to elicit a biological response. An antagonist is described herein as any ligand that results in the inverse response to an agonist while an inhibitor is any agent that blocks the biological response generated by the agonist. An inverse agonist is a drug which acts at the same receptor as that of an agonist, yet produces an opposite effect. Inverse agonists are also referred to as negative antagonists.

Suitably, the agent is selected from the group consisting of organic molecule, inorganic molecule, ion and environmental stimulus. Preferably, the organic molecule is selected from the group consisting of peptide, polypeptide, nucleotide, polynucleotide, protein nucleic acid, saccharide, polyglyceride and small organic molecule.

Suitably, the method is conducted on a cellular membrane fraction. The method may also be conducted on living, intact cells.

The present invention offers advantages over those methods known in the art by employing site-specific labelling of G-protein subunits, which are generic to a range of G-protein subtypes, and which circumvents one of the key problems associated with studies involving singular reporting with labelled GTP analogues alone. These latter approaches can and do suffer from high "basal" (or "background") rates of exchange of GTP for GDP in the absence of a GPCR ligand (Milligan (2003) Trends in Pharm. Sci., 24, 87-90). In addition, other membrane proteins, such as tubulin, can exchange GTP for GDP. Thus, in the absence of ligand, there will be a fixed degree of basal cellular labelling, such as on the Gα subunit of the G-proteins. What this can mean is that when a specific GPCR ligand is subsequently added, the ligand "effect" of GTP analogue recruitment to the Gα subunit can be "masked" by the high endogenous basal exchange, resulting in a poor signal to background. Basal binding is biased due to high expression levels of the $G_i$ family of G-proteins in mammalian cell systems, as well as higher rate of basal GTP exchange at the $Gα_i$ subunits relative to other Gα-protein families ($G_s$ and $G_q/G_{12,13}$). In many cell membranes and cellular systems employed in the art, there is always going to be a mixed population of G-protein families, reflecting combinations of relative expression levels. It thus becomes very difficult to measure specific ligand-based activation of the $Gα_s$ and $Gα_q/Gα_{12,13}$ G-proteins, which constitute a very important aspect of GPCR activity and hence potential therapeutic intervention, because of the masking effect.

A key aspect of the present invention is that a secondary reporter moiety is directed onto a G-protein subunit of a specific family (e.g. $Gα_q$), via a site-specific covalent tag. This will allow FRET reporting activity only at that $Gα_q$-protein family to be recorded. This is because the positive FRET signal, after addition of a $Gα_q$-active ligand, will only be generated when the reporter fluor on the specific $Gα_q$-protein comes into close proximity with the secondary fluor on the GTP analogue (e.g. FIG. 2). In the absence of ligand, although the other G-proteins (e.g. $Gα_s$ and $Gα_i$) may have experienced high rates of basal GTP exchange (and hence be "labelled" by the GTP-fluor analogue), no FRET signal will be generated from these latter basal interactions. In yet another manifestation of FRET interactions, a choice of FRET partners may allow time-resolved analysis which may confer advantages depending on the type of study under investigation. Suitable dyes for time-resolved analysis include the acridone class of dyes, as described in WO 02/099424, and the quinacridone class of dyes as described in WO 02/099432.

The prior art methods described above do not show site specificity, and are not generic in the sense that a non-covalently bound affinity probe or antibody (for example) would have to be sourced and screened for, in every case. In these latter cases, these alternative probes may well have varying affinities for their targets. When screening for samples with mixed target populations (as could be the case for Gα) having probes with varying affinity may well "misreport" this population difference due to biasing of binding towards the higher strength binders.

The use of a single covalently bound tag (or probe) in the method of the present invention circumvents many of the problems associated with sourcing and testing non-covalently bound probes. Having a covalently bound probe removes the likelihood of perturbation of probe-target interactions, which is a risk when non-covalent probes are employed. These perturbations may arise from non-optimised assay conditions or from exogenous test compounds, leading to false positives or negatives.

Thus use of a generic and covalent tag allows for facile modifications of the reporter system, thus introducing an element of versatility into choice of reporters and detection systems as well as allowing optimisation of both the labelling content and the concentrations of the components.

The method of the present invention offers further advantages over the prior art methods in that it is both fluorescent and homogeneous in nature, requiring no separation steps, thus conferring convenience and sensitivity.

In a fourth aspect of the present invention there is provided a nucleic acid construct comprising a nucleic acid sequence encoding a Gα subunit polypeptide comprising a GTP binding site and the means to ligate, by chemical or enzymatic methods, a covalently bound first detectable group as hereinbefore described.

According to a fifth aspect of the present invention, there is provided a vector comprising the nucleic acid construct as hereinbefore described. Suitably, the vector is a plasmid or a viral vector. Preferably, the viral vector is an adenoviral vector or a lentiviral vector.

In a sixth aspect of the present invention, there is provided a cell transfected with a vector as hereinbefore described. If the vector is a plasmid vector, transfection can be achieved by methods which are well known in the art, such as DNA compaction, electroporation and the use of chemical carriers. If the vector is a viral vector, transfection is achieved by exploitation of the virus coat transfection recognition motifs targeting onto the host cell.

FIG. 5 illustrates the process by which suitable host cells can be transfected with a viral vector according to the invention. In the example give, intein-mediated site-specific biotynlation of the Gα subunit is employed using the in vivo approach described by Lue et al. (J.Am.Chem.Soc. (2004) 126, 1055-1062). Cells are transfected with a shuttle vector, comprising a DNA encoding a Gα-intein subunit, and a vector comprising viral DNA (see, for example, U.S. Pat. No. 6,140,087) to produce non-replicative viral particles containing DNA encoding for the Gα-intein subunit. The cells are further transfected with cDNAs encoding GPCR, Gβ and Gγ subunits. In vivo intein-mediated biotinylation of the Gα subunit is achieved by the addition of a cysteine-containing biotin tag to the cells. The resulting cells comprise functional Gα, Gβ and Gγ subunits and GPCR polypeptide.

Suitably the cell is either a stable cell line or a transient cell line. The term 'stable cell line' is used to describe a cell line where the foreign DNA from the vector has been stably integrated into the cell genome and is replicated upon cell division, such that daughter cells also posses the foreign DNA. In contrast, a 'transient cell line' is a cell line in which the DNA has not been stably integrated into the genome, is only expressed in the transformed cell and is not replicated upon cell division.

Suitably, the cell further expresses a Gβ GPCR subunit and a Gγ GPCR subunit.

Preferably, the cell is eukaryotic cell. Most preferably, the cell is a mammalian cell.

In a seventh aspect of the present invention, there is provided a Gα subunit polypeptide encoded by the nucleic acid as hereinbefore described or produced by the host cell as hereinbefore described.

In a eighth aspect of the present invention, there is provided a kit of parts comprising a Gα subunit polypeptide according to the seventh aspect of the invention and a GTPase resistant GTP analogue having a second detectable group, or a GTPase resistant GTP analogue having a second tag capable of binding to a second detectable group.

Preferably, the kit further comprises a first detectable group which is Cy3B-streptavidin. More preferably, the second detectable group is Cy5.

In a ninth aspect of the present invention, there is provided a kit of parts comprising a vector according to the fifth aspect of the invention, and a GTPase resistant GTP analogue having a second detectable group, or a GTPase resistant GTP analogue having a second tag capable of binding to a second detectable group.

Preferably, the kit further comprises a first detectable group which is Cy3B-streptavidin. More preferably, the second detectable group is Cy5.

BRIEF DESCRIPTION OF THE DRAWINGS

FIG. 4a shows the nucleic acid sequence (SEQ ID NO: 1) encoding a Gα subunit according to the present invention.

FIG. 4b shows the amino acid sequence (SEQ ID NO: 2) of a Gα subunit according to the present invention.

DETAILED DESCRIPTION OF THE INVENTION AND EXAMPLES

Figure 1:
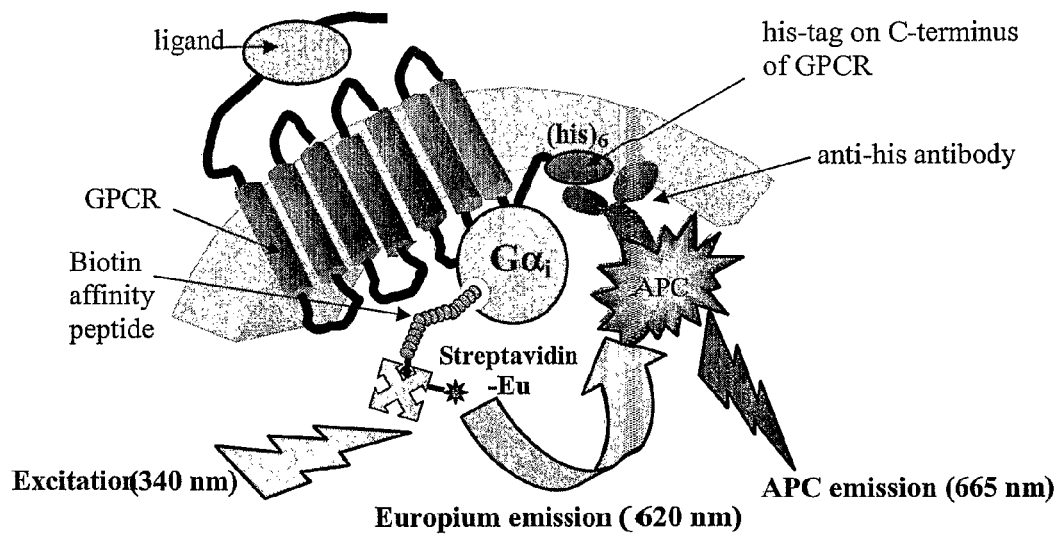
FIG. 1 illustrates a prior art 'intermolecular' FRET assay for GPCR ligand binding.
Figure 2:
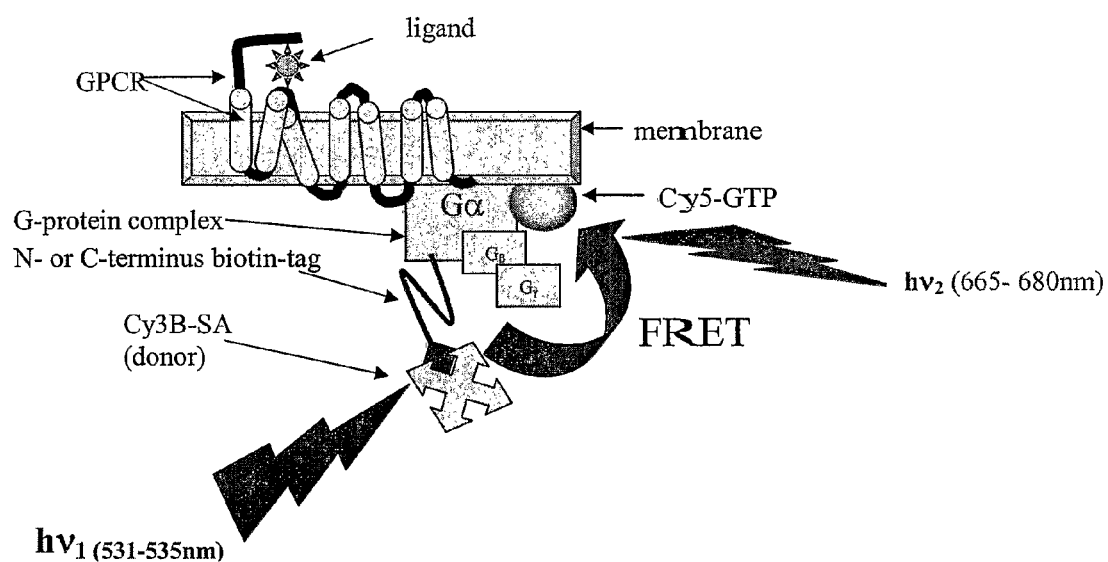
FIG. 2 is a schematic representation of a FRET assay according to the present invention.

The invention is illustrated by reference to the following examples. The present examples are provided for illustrative purposes only, and should not be interpreted in any way as limiting the scope of the invention as defined by the appended claims. All references provided below and elsewhere in the present specification are hereby included herein via reference.

1. Synthesis of Cy5 Labelled GTP Analogue: Cy5-C2-GTP (Compound 1 or Formula I Above)

1.1 Synthesis of $O^5$-[3-(2-aminoethylamino)-1,2,3-trihydroxy-triphosphoryl-guanosine: Compound 2

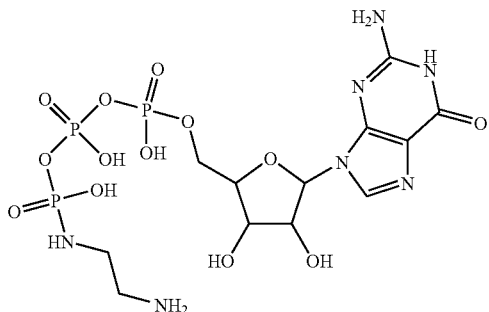

The tetra-lithium salt of GTP (25 mg, 0.048 mmol) and N-(3-dimethylaminopropyl)-N'-ethylcarbodiimide hydrochloride (36 mg, 0.190 mmol) were dissolved in 4 ml of 0.1 M triethanolamine hydrochloride buffer (pH 7.2) in a 25 ml round-bottomed flask fitted with a magnetic stirrer bead. N-Fmoc-ethane-1,2-diamine hydrobromide (113 mg, 0.31 mmol) was suspended in 1.5 ml of 1,4-dioxan and added to the stirred solution in the flask. DMF was added dropwise to the suspension in the flask until it became homogeneous. The solution was stirred at ambient temperature under an atmosphere of nitrogen for 20 hours. TLC(RP-18, 40:60 methanol: water) showed that all the GTP had reacted. The solution was evaporated to dryness under vacuum. 2.5 ml of a mixture of 20:80 piperidine:DMF was added to the residue and the mixture stirred at ambient temperature for 15 minutes. The solution was then evaporated to dryness under vacuum. The residue was dissolved in water (10 ml) and extracted with diethyl ether (2×10 ml), the aqueous phase was then evaporated to

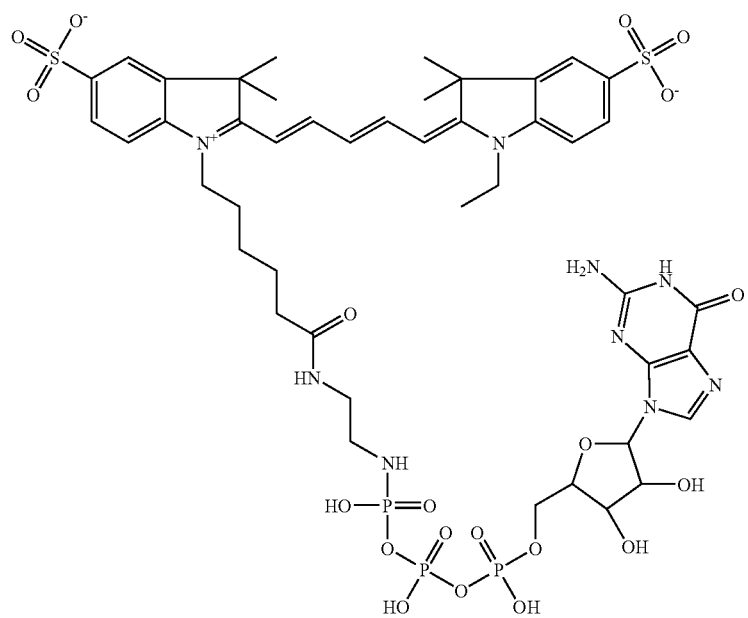

dryness under vacuum. TLC (RP-18, 40:60 methanol:water) showed a single spot ($R_f$ 0.75) which turned purple when sprayed with ninhydrin.

The residue was dissolved in water and purified by HPLC using a MonoQ™ 10/10 column (Amersham Biosciences) eluting with a gradient of water to 100% 0.5M triethylammonium acetate solution (pH 7.0) over 60 minutes at a flow of 3 ml/minute. Detection was at 260 nm. The major product eluted after 36 minutes. This material was evaporated to dryness under vacuum and the residue dissolved in a minimal volume of water. This was further purified by reverse phase HPLC using a 250×10 mm Jupiter™ C-18 column (Phenomenex) eluting with 0.1M triethylammonium acetate solution (pH 7.0) at a flow of 4 ml/minute. Detection was at 260 nm. A single peak eluted after 11.3 minutes. This material was evaporated to dryness under vacuum, the residue was dissolved in water and the process repeated several times to remove as much triethylammonium acetate as possible to give compound (2) as a colourless solid.

Mass spectrometry (ES$^+$) gave MH$^+$ at 566 and MNa$^+$ at 588. ($C_{12}H_{22}N_7O_{13}P_3$ requires 565). Calculated yield from absorption at 253 nm was 7.1 mg (0.012 mmol, 25%)

1.2 Synthesis of Cy5 Labelled GTP Analogue: Cy5-C2-GTP (Compound 1)

Compound 2 (2 μmol) was dissolved in 0.2 ml of water in a 1.5 ml polypropylene V-vial. To this was added 100 μl 0.1M sodium bicarbonate solution followed by 200 μl of a solution of 10 mg (14.4 μmol) Cy5-NHS ester in 1 ml dry DMSO. The tube was placed on roller for 20 hours at ambient temperature. This material was purified by reverse phase HPLC using a 250×10 mm Jupiter C-18 column (Phenomenex) eluting with a gradient of 0.1M triethylammonium acetate solution (pH 7.0) to 50% acetonitrile over 30 minutes at a flow of 4 ml/minute. Detection was at 650 nm. The component eluting after 20 minutes was collected, then evaporated to dryness under vacuum to give compound 1 as a blue solid.

Mass spectrometry (ES$^+$) gave MNa$^{2+}$ at 614.7 and MNa$^+$ at 1228.3 ($C_{45}H_{60}N_9O_{20}P_3S_2$ requires 1203)

Calculated Yield from Absorption at 649 Nm was 0.56 Mg (0.46 μMol, 23%)

2. Synthesis of Cy5 Labelled GTP Analogue: Cy5-C6-GTP (Compound 3 or Formula II Above)

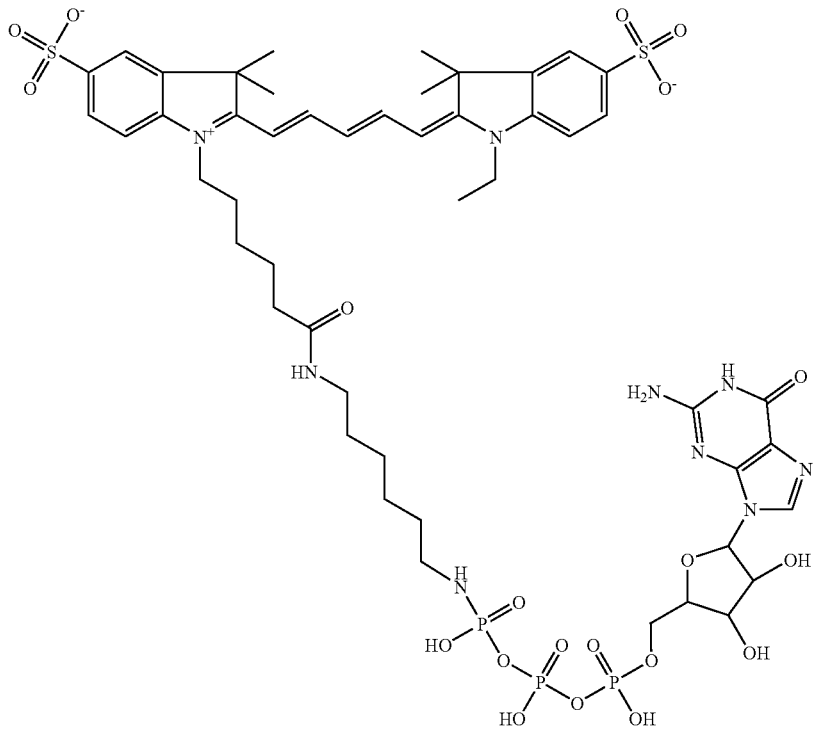

2.1 Synthesis of $O^5$-[3-(6-aminohexylamino)-1,2,3-trihydroxy-triphosphoryl-guanosine: Compound 4

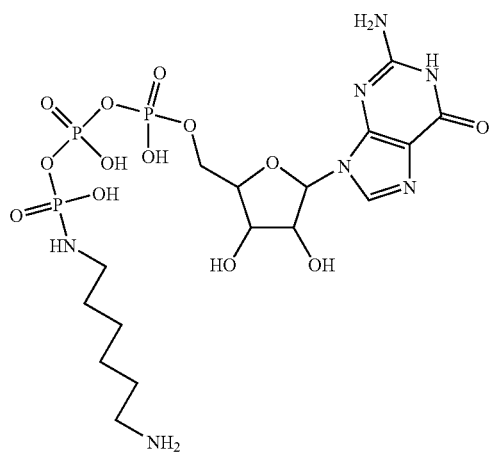

The tetra-lithium salt of GTP (25 mg, 0.048 mmol) was dissolved in 2 ml of 0.1M triethanolamine hydrochloride buffer (pH 7.2) in a 25 ml round-bottomed flask fitted with a magnetic stirrer bead. To this was added N-Fmoc-hexane-1,6-diamine hydrobromide (42 mg, 0.10 mmol) dissolved in 1 ml dry DMF. N-(3-dimethylaminopropyl)-N'-ethylcarbodiimide hydrochloride (72 mg, 0.37 mmol) was dissolved in 1 ml of the triethanolamine buffer and added to the stirred solution in the flask. DMF was added dropwise to the suspension in the flask until it became homogeneous. The solution was stirred at ambient temperature under an atmosphere of nitrogen for 20 hours. TLC (RP-18, 40:60 methanol:water) showed that some of the GTP had still not reacted. A further portion of N-(3-dimethylaminopropyl)-N'-ethylcarbodiimide hydrochloride (72 mg, 0.37 mmol) was added and stirring was continued for a further 20 hours. The solution was evaporated to dryness under vacuum. 5 ml of a mixture of 20:80 piperidine:DMF was added to the residue and the mixture stirred at ambient temperature for 15 minutes. The solution was then evaporated to dryness under vacuum.

The residue was dissolved in water (10 ml) and extracted with diethyl ether (2×10 ml), the aqueous phase was then evaporated to dryness under vacuum. TLC (RP-18, 40:60 methanol:water) showed a single spot ($R_f$-0.75) which turned purple when sprayed with ninhydrin. The residue was dissolved in water and purified by HPLC using a MonoQ 10/10 column (Amersham Biosciences) eluting with a gradient of water to 100% 0.5M triethylammonium acetate solution (pH 7.0) over 60 minutes at a flow of 3 ml/minute. Detection was at 260 nm. The major product eluted after 22 minutes. This material was evaporated to dryness under vacuum and the residue dissolved in a minimal volume of water. This was further purified by reverse phase HPLC using a 250×10 mm Jupiter C-18 column (Phenomenex) eluting with a gradient of 0.1M triethylammonium acetate solution (pH 7.0) to 40% acetonitrile over 40 minutes at a flow of 4 ml/minute. Detection was at 260 nm. A single peak eluted after 25 minutes. This material was evaporated to dryness under vacuum, the residue dissolved in water and the process repeated several times to remove as much triethylammonium acetate as possible to give compound 4 as a colourless solid.

Mass spectrometry (ES$^+$) gave MH$^+$ at 622.21. ($C_{16}H_{30}N_7O_{13}P_3$ requires 621.4)

Calculated yield from absorption at 253 nm was 3.5 mg (0.007 mmol, 15%)

2.2 Synthesis of Cy5 Labelled GTP Analogue: Cy5-C6-GTP (Compound 3)

Compound 4 (2.3 µmol) was dissolved in 0.2 ml of water in a 1.5 ml polypropylene V-vial. To this was added 200 µl 0.1M sodium bicarbonate solution followed by 300 µl of a solution of 10 mg (14.4 µmol) Cy5-NHS ester in 1 ml dry DMSO. The tube was placed on roller for 20 hours at ambient temperature. The material was purified by ion exchange HPLC (Hiprep™ 16/10 DEAE FF column). The column was eluted with water from 0-9 minutes, then water to 35% 2M sodium chloride from 9-40 minutes at a flow rate of 5 ml/minute. Detection was at 253 and 650 nm. The major product eluted after 28 minutes. This material was de-salted by reverse phase HPLC using a 250×10 mm Jupiter C-18 column (Phenomenex) eluting with 0.1M triethylammonium acetate solution (pH 7.0) at a flow of 4 ml/minute. Detection was at 253 and 650 nm. The major component was collected then evaporated to dryness under vacuum to give compound 3 as a blue solid.

Mass spectrometry (ES$^+$) gave MH$^+$ at 1260.3. ($C_{49}H_{67}N_9O_{20}P_3S_2$ requires 1258.3)

Calculated yield from absorption at 649 nm was 0.7 mg (0.6 µmol, 26%)

3. Synthesis of Streptavidin Labelled Cy3B: Cy3B-Streptavidin

Streptavidin (10 mg; Rockland Immunochemicals; S000-01; 16.3 U/mg) was dissolved in NaHCO$_3$ buffer (2.5 ml; 0.1 M; pH 9.2).

The concentration of the solution was measured by UV spectroscopy ($E_{280}^{0.1\%}$=3.17; concentration (mg/ml)= (OD$_{280}$× dilution factor)/3.17) then adjusted by addition of NaHCO$_3$ buffer to form a concentration of 2 mg/ml. Cy3B NHS ester (2 mg; Amersham Biosciences; PA63100) was dissolved in DMF (0.4 ml) then added to the streptavidin solution and stirred at room temperature for 1 h. The reaction mixture was transferred to a pre-soaked Slide-A-Lyzer® dialysis cassette (3-15 ml; Pierce Biotechnology; 66425; 10K MW cutoff) and dialysed (0.15 M NaCl; 4×2 l then 0.1 M PBS-azide; pH 7.2; 4×2 l) at 4° C. for 48 h. The dye:protein ratio was determined by UV spectroscopy using the following equation:

$$\text{Dye:Protein ratio} = \frac{A_{564}/130000}{A_{280} - (A_{564} \times 0.5)/200000}$$

to give 3.3 dyes/protein

[Cy3B$\lambda_{max}$=564 nm; $\epsilon_{564}$=130000 M$^{-1}$ cm$^{-1}$; correction factor=0.05; streptavidin $\epsilon_{280}$=200000 M$^{-1}$ cm$^{-1}$; correction factor=0.05]

The concentration of the solution was adjusted to 1 mg/ml with PBS azide buffer and BSA [100 mg, Rockland Immunochemicals; BSA-10] was added. After stirring for 5 min, 1 ml aliquots were dispensed into P87 vials and the product was isolated after freeze drying.

4. Preparation of Gα Subunits

Preparation of tagged Gα subunits by biological means can be carried out by a variety of methods known to those familiar with the art of cDNA cloning, creating vector constructs from this cDNA, transfecting a suitable host cell with the latter construct and generating the required target protein. Many of the processes described above can be carried out by use of commercially available reagents and "kits".

4.1 Preparation of Isolated Gα Subunits

In a typical example, where Gα is to be tagged with biotin and the biotin-Gα is required as an isolated product, the following procedure can be carried out:

The required cDNA for Gα ("gene of interest") can be obtained via a gene bank repository. This gene can be cloned using established techniques into ideally, a bacterial host (for example, a "midi-prep" procedure in *E. coli* host bacteria). A commercially available vector can be used for the required tag, and the use of restriction enzymes and ligases allows insertion of the gene of interest into the vector to create a vector-plasmid construct. This vector-plasmid construct can be further transformed into competent bacterial host cells (for example TOP 10 *E. coli*) for long-term storage on beads.

Figure 3:
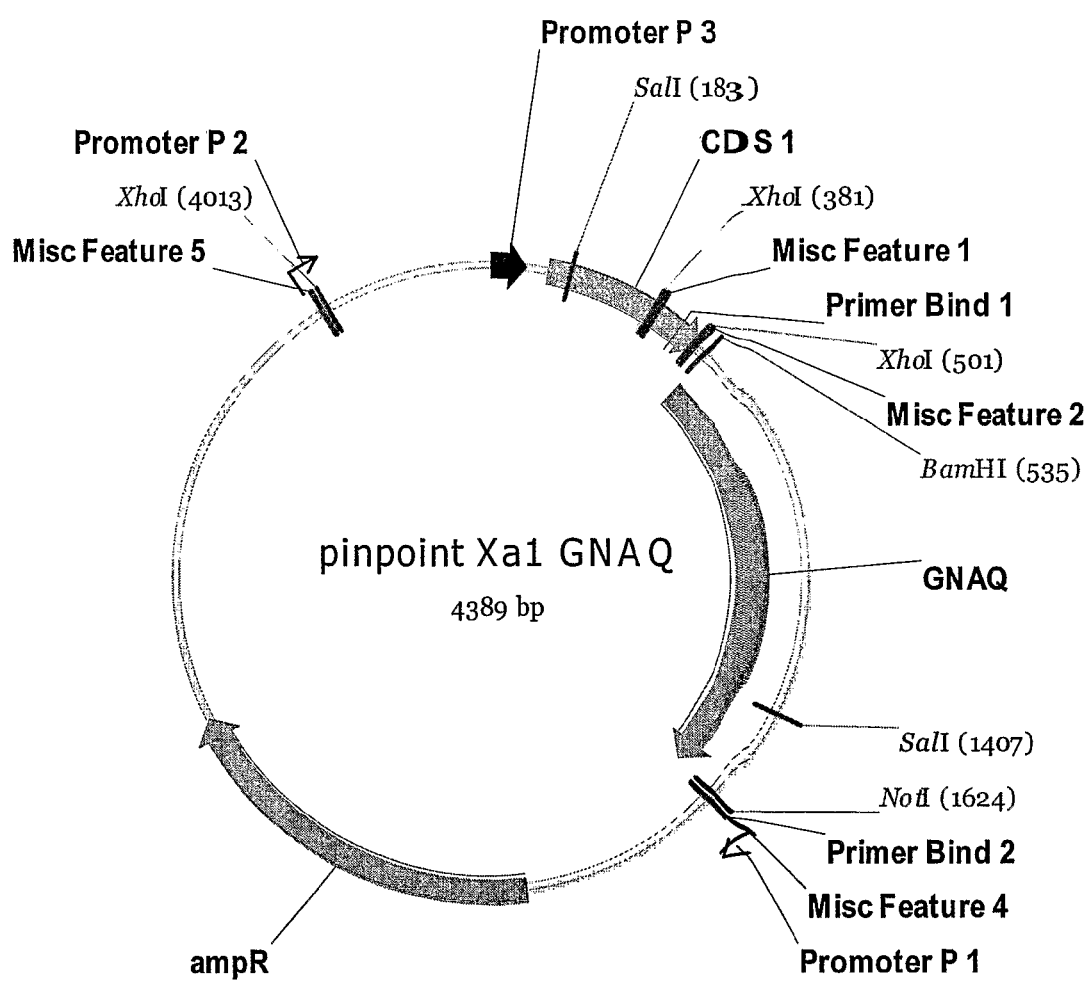
FIG. 3 is a plasmid vector map comprising a nucleic acid encoding a Gα subunit according to the present invention.
Figure 5:
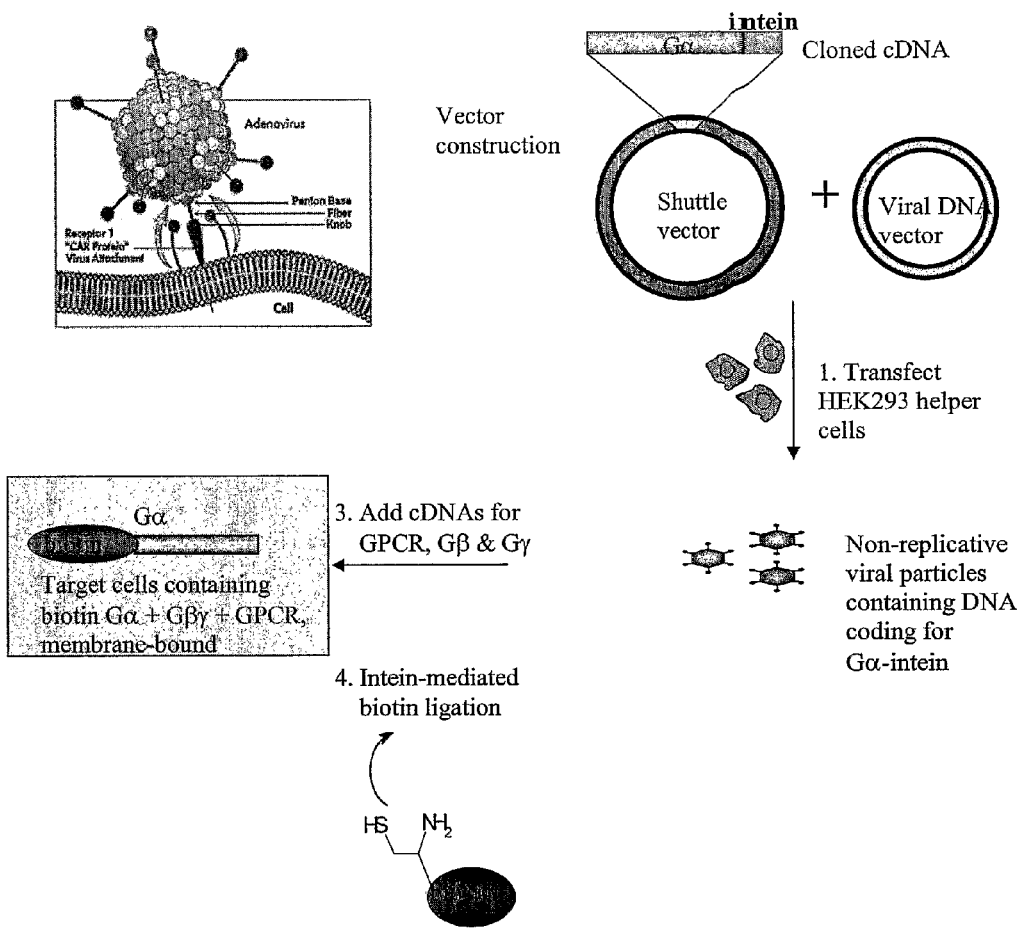
FIG. 5 is a schematic representation of a method of viral infection of a host cell and in vivo intein-mediated biotinylation of a Gα subunit according to the present invention.

FIG. 3 shows a plasmid vector according to the present invention used to transfect HEK 293 cells. The PinPoint™ Xa vector (Promega Corporation) was used to effect expression of biotin-tagged Gα$_q$ subunit in *E. coli*. The DNA encoding the Gα$_q$ subunit was inserted downstream from the sequence encoding the Gα$_q$ subunit that is biotinylated in vivo as the fusion protein is expressed. The recombinant plasmid was transformed in *E. coli* and protein production was induced by IPTG. FIG. 4a & b show the nucleic acid and amino acid sequences of the Gα$_q$ subunit. To generate the required tagged Gα protein of interest (e.g. Gα$_q$) a bead containing the adsorbed transformed bacterial host cells is allowed to grow using established methods (e.g. antibiotic selection procedures). Resistant clones are manually selected and allowed to expand into large scale (for example up to 1 liter) culture vessels in the presence of biotin. The culture broth is spun down and stored as a pellet. To isolate the desired tagged protein, an aliquot of the pellet is treated with a suitable lysis reagent, with or without ultra-sonication, followed by a two-stage purification procedure. The first stage is by use of commercially-available biotin affinity monomeric avidin resins and the second stage is by size exclusion chromatography. The desired end product (e.g. biotin-tagged Gα) can be assessed for purity by traditional means, such as by gel electrophoresis and for protein concentration, using commercially-available protein assay kits.

4.2 Preparation of Integral Gα Subunits

In a typical example where Gα is to be tagged with biotin, and the biotin-Gα is required as an integral part of an intact GPCR receptor system together with the associated G-proteins, the following procedure can be carried out:

The required cDNA for Gα "gene of interest" can be obtained via a gene bank repository. A gene construct (for example, Gα-intein, where the intein is preferably ligated onto the N-terminus of Gα), is cloned into a mammalian expression vector using standard commercially-available technology. Suitable mammalian host cells (for example, HEK 293 cells) are transiently transfected with the vector using commercially available chemical transfection technology.

Alternatively, transfection may be carried out using viral delivery, where the viral particles would contain the intein-Gα cDNA constructs. Viral delivery allows potentially higher transfection efficiency rates.

Preferably, the host cells will contain cDNAs allowing constitutive expression of a desired GPCR system including associated G-proteins, ion-channels etc. In addition, there may be introduced methods of "repression", or "silencing" the endogenous Gα of the host cell genome so as to allow full expression of the exogenous tagged Gα protein. As an example, "null" mutants of Gα do exist which could be employed. After a suitable incubation period in selected growth media and under controlled conditions, tagging reagents are added (for example, a derivatised biotin-thioester) to the medium. Mammalian cells are then harvested and lysed under controlled conditions to generate membrane fragments which can be stored for later use in GPCR assays. The latter fragments will contain membrane-associated GPCR and associated G-proteins, where Gα carries a suitable tag, and which should allow fully reconstituted GPCR activity to be monitored in the presence and absence of modulating agents, such as drugs, ions and environmental changes.

5. Assay Methods for Measuring Ligand Binding to GPCR 5.1 Assays Involving Isolated Gα Subunits In a typical example where Gα is to be tagged with biotin, and the biotin-Gα is required as an isolated product for optimisation experiments (e.g. to optimise dye concentrations in a FRET assay format), the following procedure can be carried out:

The assay is set up in black 96-well microtitreplates, usually to obtain data sets of triplicate values, in a final reaction volume of 100 µl. The concentrations of the 3 key components are as follows:

Biotin-Gα subunit, purified (MW ~40,000 to 48,000, typically 4 pmol/well), "donor" Cy3B-streptavidin (typically 20 nM final) (2 pmol/well) and "acceptor" Cy5-GTP (typically 40 nM; 4 pmol/well final). The binding buffer employed is typically 20 mM HEPES, 3 mM $MgCl_2$, 100 mM NaCl+100 µg/ml saponin, pH 7.5. Other buffers can include TRIS, with varying concentrations of $MgCl_2$, NaCl and detergents.

To the assay plate wells is added assay buffer (60 µl 100 µl), followed by biotin-Gα 10 µl) (4 pmol/well) and, where appropriate, GTPγS; (10 µl) (typically 100 µM; 10 µM final) (for non-specific binding "NSB" wells), Cy3B-SA (10 µl) (200 nM, 20 nM; 2 µmol final), Cy5-GTP (10 µl) (400 nM, 40 nM; 4 pmol final). The plate is gently shaken on a plate shaker for 30-45 minutes at room temperature.

Detection is carried out in a fluorescent Plate detector, with filter settings at 531 nm (excitation, bandwidth 25 nm) and 665 nm (emission, bandwidth 7.5 nm).

Figure 6:
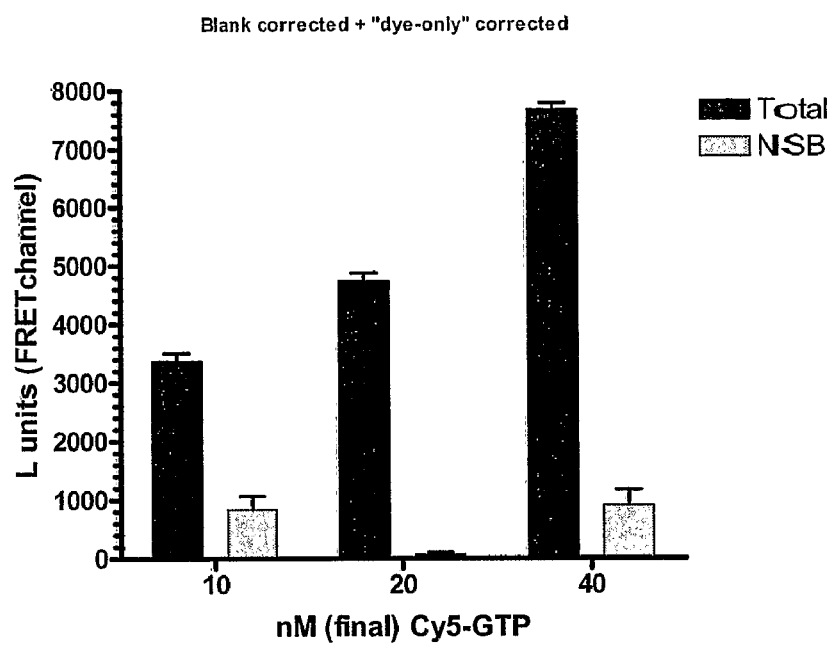
FIG. 6 displays typical results from a FRET assay according to the present invention.

FIG. 6 shows the result of a typical experiment carried out with 2 pmol/well of Cy3B and 2 pmol/well of Gα subunit and a concentration range of Cy5-GTP (1-4 pmol/well). As can be seen, increasing the concentration of the Cy5-GTP acceptor results in an increasing fluorescent signal.

In this assay there is no associated membrane present nor accompanying integral GPCR. Therefore ligand binding events or perturbation of those events by agents, for example, cannot be carried out in this isolated and "decoupled" system. However, the assay can be used to test (for example) the integrity of the FRET system or to optimise concentrations of the FRET dyes, and so presents a useful approach to rational assay design.

5.2 Assays Using Integral Gα Subunits

In a typical example, where Gα is to be tagged with biotin and the biotin-Gα is required as an integral part of an intact GPCR receptor system together with the membrane-associated G-proteins, the following assay can be carried out using, for example, cell-membrane extracts:

The assay is set up in black 96-well microtitreplates, usually to obtain data sets of triplicate values, in a final reaction volume of 100 µl. A reference ligand (10 µl) is plated out into appropriate wells at a suitable final concentration range of typically 1-100 nM. In the same wells is added either zero agent (10 µl buffer only) or an increasing concentration of agent (10 µl; typically a range of 1 nM-10 µM). Chosen microtitreplate wells will also contain excess non-labelled GTPγS (10 µl) (typically 100 µM; 10 µM final) to assess the degree of non-specific binding (NSB). Membrane containing fully reconstituted GPCR of interest with associated G-proteins (typically 1-4 pmol receptor/well), part of which will consist of biotin-tagged Gα subunit (10 µl) is added. This is followed by "donor" Cy3B-streptavidin (10 µl) (typically 20 nM final; 2 pmol/well) and "acceptor" Cy5-GTP (10 µl) (typically 40 nM final; 4 pmol/well). Volume of the wells is made up to 100 µl with assay binding as appropriate. The binding buffer typically employed is 20 mM HEPES, 3 mM $MgCl_2$, 100 mM NaCl+100 µg/ml saponin, pH 7.5. Other buffers can include TRIS, with varying concentrations of $MgCl_2$, NaCl and detergents.

The plate is gently shaken on a plate shaker for 45 minutes at room temperature. These conditions can vary. Detection is carried out in a fluorescent plate detector, with filter settings at 531 nm (excitation, bandwidth 25 nm) and 665 nm (emission, bandwidth 7.5 nm).

This assay, with fully integrated and reconstituted GPCR containing biotin-tagged Gα, allows rank order of potency profiling of a range or agents when measured against a reference ligand or group of reference ligands.

It will be understood that the skilled person can use this assay to generate panels of any reconstituted GPCR of interest with combinations of Gα, Gβ and Gγ subunits, where the Gα is specifically tagged as herein before described.

If this GPCR of interest is a GPCR whose associated endogenous ligands are unknown (the so-called "orphan" receptors), then by use of appropriately-sourced cDNA to generate reconstituted GPCR and associated G-proteins with incorporated tagged-Gα, the assay method allows the "screening" of that GPCR and assignment of function to a particular endogenous ligand chosen from a "pool" of biological extracts from a relevant source. This process of assignment of endogenous ligand to a GPCR which has previously unknown associated endogenous ligands, is known as "de-orphanisation". The assay method further allows assignments of endogenous ligands with the most noted biological effects to a particular GPCR. This information on both the target GPCR as well as its endogenous ligands, allows a more rational approach to improved understanding of the pharmacology of the GPCR and associated biological pathways, a clearer understanding of the role of the GPCR/endogenous ligand in a disease process, and a more rational approach to drug design.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

The invention claimed is:

1. A method for detecting binding of a test compound to a G-Protein Coupled Receptor (GPCR), said method comprising (A) the steps of:
   i) contacting the GPCR with the test compound;
   ii) contacting a Gα subunit of said GPCR, which comprises a covalently bound tag capable of binding to a first detectable group, with a GTPase resistant GTP analogue having a second detectable group;
   iii) binding the first detectable group to the covalently bound tag, wherein the first detectable group and the second detectable group comprise fluorescent moieties which form a fluorescence resonance energy transfer FRET pair; and
   iv) detecting a signal by optical means to measure the level of interaction between the first detectable group and the second detectable group; or (B) the steps of:
   i) contacting the GPCR with the test compound;
   ii) binding a first detectable group to a tag;
   iii) contacting a Gα subunit of said GPCR, which comprises the covalently bound tag, with a GTPase resistant GTP analogue having a second detectable group, wherein the first detectable group and the second detectable group comprise fluorescent moieties which form a fluorescence resonance energy transfer FRET pair; and
   iv) detecting a signal by optical means to measure the level of interaction between the first detectable group and the second detectable group; and wherein said signal results from the intramolecular interaction between the first detectable group and the second detectable group; further wherein said first detectable group comprises a binding moiety which specifically binds to the tag; and further wherein the GTPase resistant GTP analogue is a compound having a formula selected from:

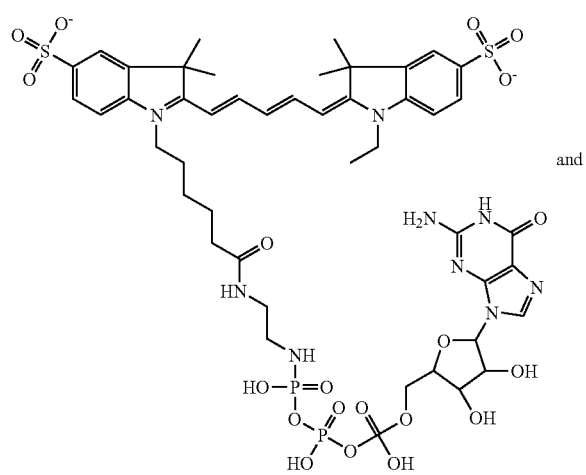

and

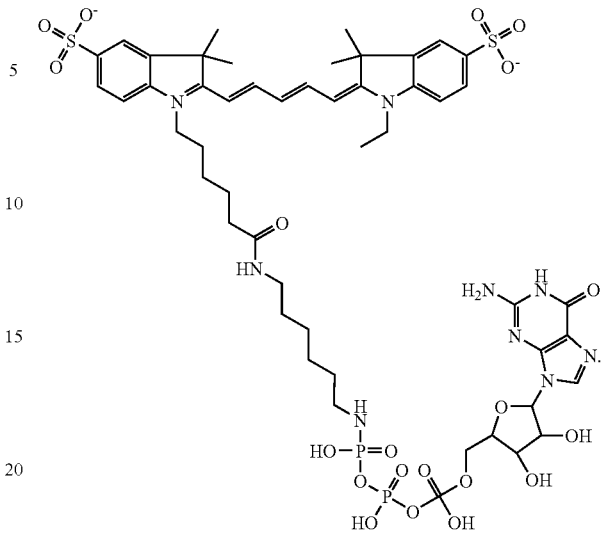

2. The method of claim 1, wherein the signal is compared to a signal obtained in the absence of the test compound.

3. The method of claim 1, wherein the test compound is a ligand.

4. The method for detecting the effect an agent has upon modulating the binding of a test compound to a GPCR, said method comprising detecting the binding of said compound to said GPCR according to the method of claim 1 in the presence of the agent and comparing binding in the absence of the agent.

5. The method of claim 1, wherein binding is measured quantitatively.

6. The method of claim 4, wherein the value of said binding in the absence of the agent is already known.

7. The method of claim 6, wherein said value of binding in the absence of the agent is stored on an electronic or optical database.

8. The method of claim 1, wherein said tag and said binding moiety are members of a specific binding pair.

9. The method of claim 8, wherein said specific binding pair is selected from the group consisting of biotin/steptavidin, biotin/avidin, biotin/neutravidin, biotin/captavidin, epitope/antibody, GST/glutathione, His tag/Nickel, FLAG/M1, maltose binding protein/maltose, chitin binding protein/chitin, calmodulin binding protein/calmodulin, and Lumio™ reagents/Lumio™ recognition sequence.

10. The method of claim 8, wherein said first tag is biotin and said binding moiety is selected from the group consisting of streptavidin, avidin, neutravidin and captavidin.

11. The method of claim 8, wherein the tag is poly histidine and the binding moiety is Nickel.

12. The method of claim 8, wherein the tag is FLAG and the binding moiety is M1.

13. The method of claim 1, wherein said FRET pair comprises a donor FRET label and an acceptor FRET label.

14. The method of claim 13, wherein said donor FRET label is a xanthine dye or a cyanine dye.

15. The method of claim 14, wherein said cyanine dye is a Cy3B dye.

16. A method for detecting binding of a test compound to a G-Protein Coupled Receptor (GPCR), said method comprising
   (A) the steps of:
   i) contacting the GPCR with the test compound;
   ii) contacting a Gα subunit of said GPCR, which comprises a covalently bound tag capable of binding to a first detectable group, with a GTPase resistant GTP analogue having a second detectable group;

iii) binding the first detectable group to the covalently bound tag, wherein the first detectable group and the second detectable group comprise fluorescent moieties which form a fluorescence resonance energy transfer pair; and iv) detecting a signal by optical means to measure the level of interaction between the first detectable group and the second detectable group; or (B) the steps of:

i) contacting the GPCR with the test compound;

ii) binding a first detectable group to a first tag;

iii) contacting a Gα subunit of said GPCR, which comprises the covalently bound tag, with a GTPase resistant GTP analogue having a second detectable group, wherein the first detectable group and the second detectable group comprise fluorescent moieties which form a fluorescence resonance energy transfer pair; and iv) detecting a signal by optical means to measure the level of interaction between the first detectable group and the second detectable group; and wherein said signal results from the intramolecular interaction between the first detectable group and the second detectable group; further wherein the first detectable group is Cy3B-streptavidin; and further wherein the GTPase resistant GTP analogue is a compound having a formula selected from:

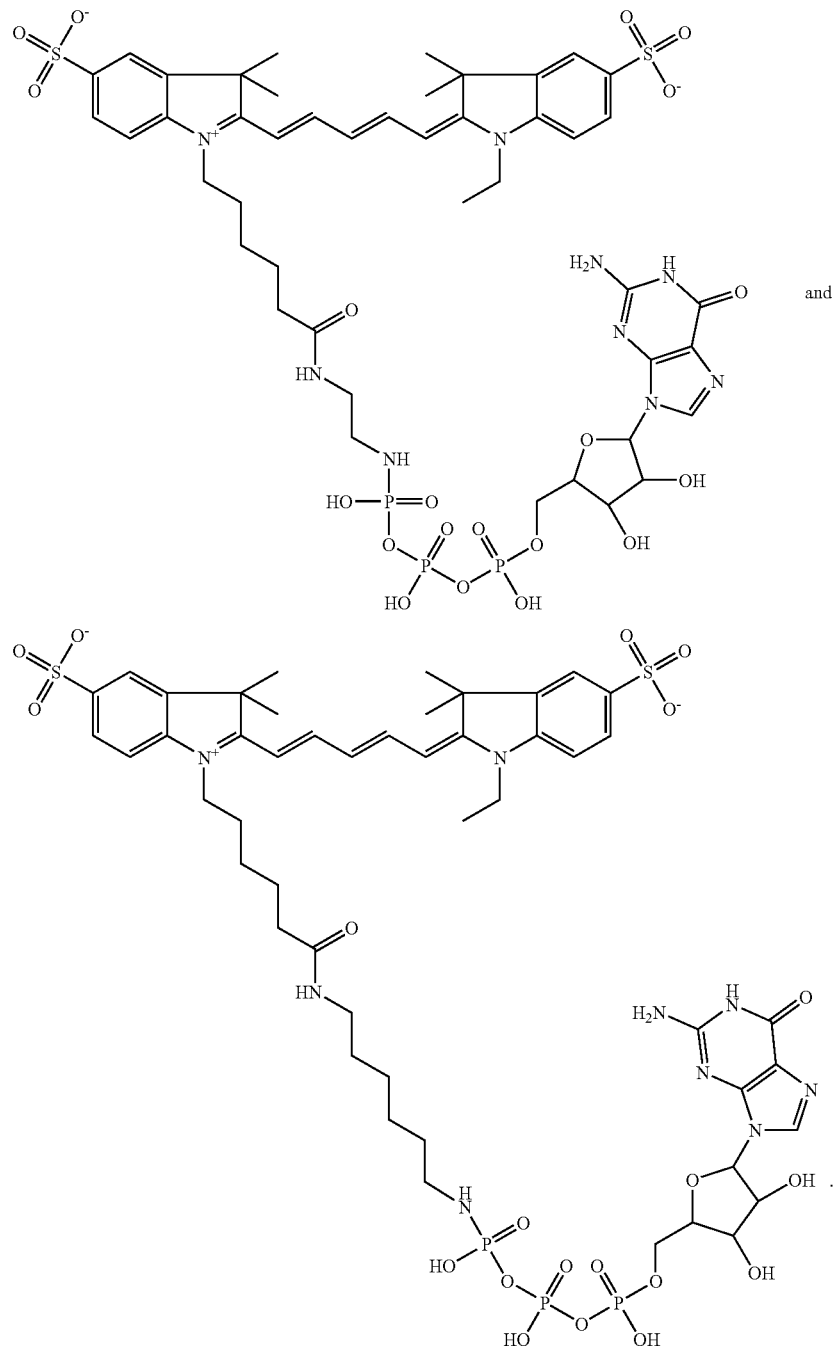

17. The method of claim 13, wherein the acceptor dye is a rhodamine dye or a cyanine dye.

18. The method of claim 13, wherein the acceptor dye is a pentamethine cyanine dye.

19. The method of claim 13, wherein the acceptor dye is Cy5.

20. A method for detecting binding of a test compound to a G-Protein Coupled Receptor (GPCR), said method comprising (A) the steps of:

i) contacting the GPCR with the test compound;

ii) contacting a Gα subunit of said GPCR, which comprises a covalently bound tag capable of binding to a first detectable group, with a GTPase resistant GTP analogue having a second detectable group;

iii) binding the first detectable group to the covalently bound tag, wherein the first detectable group and the second detectable group comprise fluorescent moieties which form a fluorescence resonance energy transfer pair; and iv) detecting a signal by optical means to measure the level of interaction between the first detectable group and the second detectable group; or (B) the steps of:

i) contacting the GPCR with the test compound;

ii) binding a first detectable group to a tag;

iii) contacting a Gα subunit of said GPCR, which comprises the covalently bound tag, with a GTPase resistant GTP analogue having a second detectable group, wherein the first detectable group and the second detectable group comprise fluorescent moieties which form a fluorescence resonance energy transfer pair; and iv) detecting a signal by optical means to measure the level of interaction between the first detectable group and the second detectable group; and wherein said signal results from the intramolecular interaction between the first detectable group and the second detectable group; further wherein the GTPase resistant GTP analogue is a compound having a formula selected from:

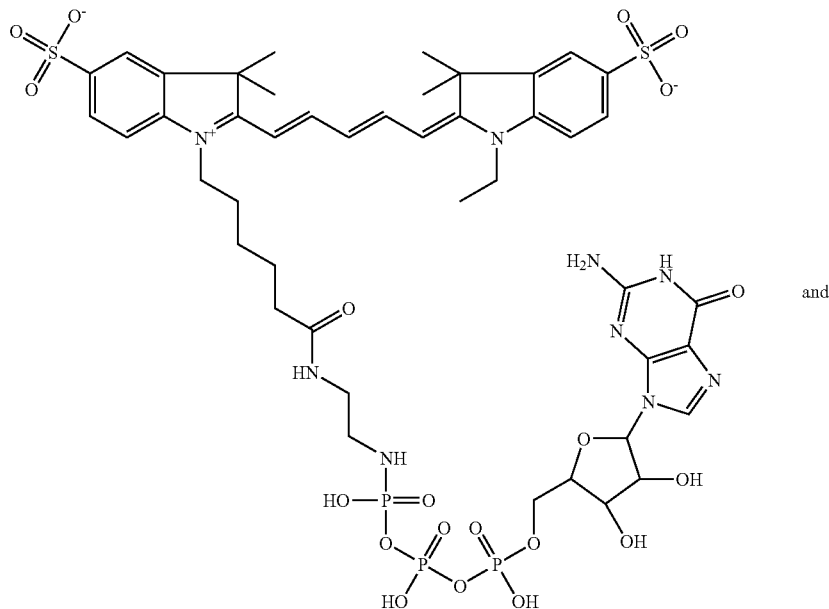

and

-continued

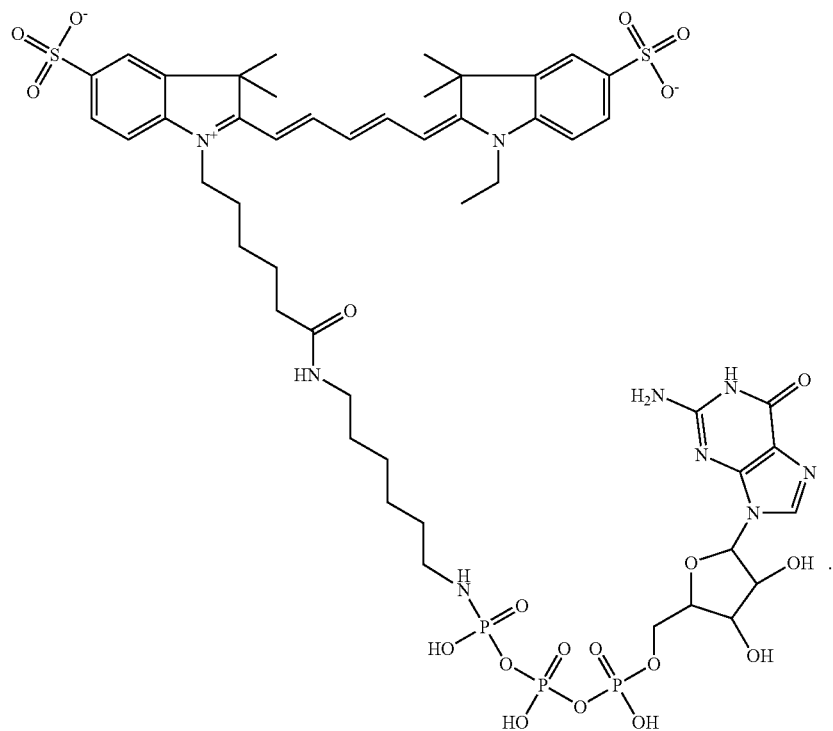

21. A method for detecting binding of a test compound to a G-Protein Coupled Receptor (GPCR), said method comprising (A) the steps of:

i) contacting the GPCR with the test compound;

ii) contacting a Gα subunit of said GPCR, which comprises a covalently bound tag capable of binding to a first detectable group, with a GTPase resistant GTP analogue having a second detectable group;

iii) binding the first detectable group to the covalently bound tag, wherein the first detectable group and the second detectable group comprise fluorescent moieties which form a fluorescence resonance energy transfer pair; and iv) detecting a signal by optical means to measure the level of interaction between the first detectable group and the second detectable group; or (B) the steps of:

i) contacting the GPCR with the test compound;

ii) binding a first detectable group to a tag;

iii) contacting a Gα subunit of said GPCR, which comprises the covalently bound tag, with a GTPase resistant GTP analogue having a second detectable group, wherein the first detectable group and the second detectable group comprise fluorescent moieties which form a fluorescence resonance energy transfer pair; and iv) detecting a signal by optical means to measure the level of interaction between the first detectable group and the second detectable group; and wherein said signal results from the intramolecular interaction between the first detectable group and the second detectable group; further wherein the covalently bound tag is biotin, and the first detectable group is Cy3B-Streptavidin; and further wherein the GTPase resistant GTP analogue is a compound having a formula selected from:

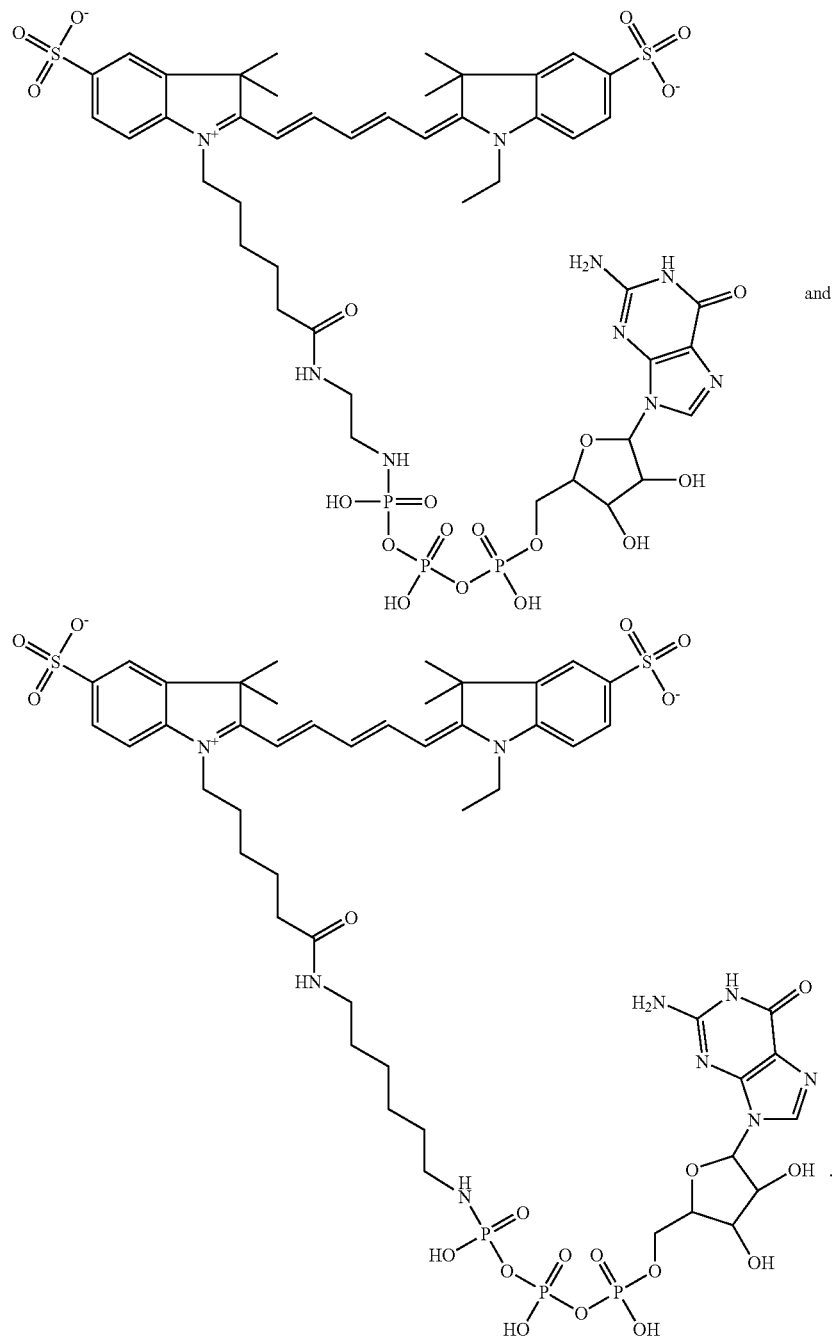

22. The method of claim 4, wherein said agent is selected from the group consisting of agonist, antagonist and inverse agonist.

23. The method of claim 4, wherein the agent is selected from the group consisting of organic molecule, inorganic molecule, ion and environmental stimulus selected from induction of changes in temperature, pressure ionic strength or pH.

24. The method of claim 23, wherein said organic molecule is selected from the group consisting of peptide, polypeptide, nucleotide, polynucleotide, saccharide and polyglyceride.

25. The method of claim 1, wherein said method is conducted on living, intact cells.

26. The method of claim 1, wherein the method is conducted on a cellular membrane fraction.

* * * * *

SEQUENCE LISTING

<160> NUMBER OF SEQ ID NOS: 3

<210> SEQ ID NO 1
<211> LENGTH: 1077
<212> TYPE: DNA
<213> ORGANISM: Artificial Sequence
<220> FEATURE:
<223> OTHER INFORMATION: Synthetic Oligonucleotide

<400> SEQUENCE: 1

```
atgactcttg aatctattat ggcttgttgt ctttctgaag aagctaaaga agctcgtcgt    60
attaatgatg aaattgaacg tcaacttcgt cgtgataaac gtgatgctcg tcgtgaactt   120
aaacttcttc ttcttggtac tggtgaatct ggtaaatcta cttttattaa acaaatgcgt   180
attattcatg gttctggtta ttctgatgaa gataaacgtg gttttactaa acttgtttat   240
caaatatttt ttactgctat gcaagctatg attcgtgcta tggatactct taaaattcct   300
tataaatatg aacataataa agctcatgct caacttgttc gtgaagttga tgttgaaaaa   360
gtttctgctt ttgaaaatcc ttatgttgat gctattaaat ctctttggaa tgatcctggt   420
attcaagaat gttatgatcg tcgtcgtgaa tatcaacttt ctgattctac taaatattat   480
cttaatgatc ttgatcgtgt tgctgatcct gcttatcttc ctactcaaca agatgttctt   540
cgtgttcgtg ttcctactac tggtattatt gaatatcctt ttgatcttca atctgttatt   600
tttcgtatgg ttgatgttgg tggtcaacgt tctgaacgtc gtaaatggat tcattgtttt   660
gaaaatgtta cttctattat gtttcttgtt gctctttctg aatatgatca agttcttgtt   720
gaatctgata atgaaaatcg tatggaagaa tctaaagctc tttttcgtac tattattact   780
tatccttggt ttcaaaattc ttctgttatt cttttttctta ataaaaaaga tcttcttgaa   840
gaaaaaatta tgtattctca tcttgttgat tatttttcctg aatatgatgg tcctcaacgt   900
gatgctcaag ctgctcgtga atttattctt aaaatgtttg ttgatcttaa tcctgattct   960
gataaaatta tttattctca ttttacttgt gctactgata ctgaaaatat tcgttttgtt  1020
tttgctgctg ttaaagatac tattcttcaa cttaatctta agaatataa tcttgtt     1077
```

<210> SEQ ID NO 2
<211> LENGTH: 359
<212> TYPE: PRT
<213> ORGANISM: Artificial Sequence
<220> FEATURE:
<223> OTHER INFORMATION: Galpha Subunit

<400> SEQUENCE: 2

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

```
Lys Arg Asp Ala Arg Arg Glu Leu Lys Leu Leu Leu Gly Thr Gly
        35                  40                  45

Glu Ser Gly Lys Ser Thr Phe Ile Lys Gln Met Arg Ile Ile His Gly
 50                  55                  60

Ser Gly Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
                100                 105                 110

Val Arg Glu Val Asp Val Glu Lys Val Ser Ala Phe Glu Asn Pro Tyr
            115                 120                 125

Val Asp Ala Ile Lys Ser Leu Trp Asn Asp Pro Gly Ile Gln Glu Cys
        130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 3
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 3

Cys Cys Pro Gly Cys Cys
1               5
```